United States Patent

Aszodi et al.

Patent Number: 5,936,083
Date of Patent: *Aug. 10, 1999

[54] CEPHALOSPORINS

[75] Inventors: Jozsef Aszodi, Choisy Le Roi; Jean-Francois Chantot, Gressy; Solange Gouin D'Ambrieres, Paris, all of France

[73] Assignee: Roussel Uclaf, France

[*] Notice: This patent is subject to a terminal disclaimer.

[21] Appl. No.: 08/625,910

[22] Filed: Apr. 1, 1996

Related U.S. Application Data

[62] Division of application No. 08/449,243, May 24, 1995, Pat. No. 5,541,318, which is a division of application No. 08/106,380, Aug. 13, 1993, abandoned, which is a division of application No. 07/987,007, Dec. 7, 1992, Pat. No. 5,397,779, which is a continuation-in-part of application No. 07/715,510, Jun. 14, 1991, abandoned.

[30] Foreign Application Priority Data

Jun. 15, 1990 [FR] France ................................... 90-07491
Dec. 12, 1991 [FR] France ................................... 91-15417

[51] Int. Cl.[6] ............................................. C07D 501/56
[52] U.S. Cl. ................................................ 540/222; 540/227
[58] Field of Search .................................. 540/225, 224, 540/222, 227

[56] References Cited

U.S. PATENT DOCUMENTS

| | | | |
|---|---|---|---|
| 5,151,417 | 9/1992 | Sasho et al. | 540/222 |
| 5,234,920 | 8/1993 | Okita et al. | 514/202 |
| 5,373,001 | 12/1994 | Aszodi et al. | 514/202 |
| 5,397,779 | 3/1995 | Aszodi et al. | 540/222 |
| 5,416,080 | 5/1995 | Aszodi et al. | 540/222 |

*Primary Examiner*—John M. Ford
*Attorney, Agent, or Firm*—Bierman, Muserlian and Lucas

[57] ABSTRACT

A compound selected from the group consisting of a syn isomer of a compound of the formula

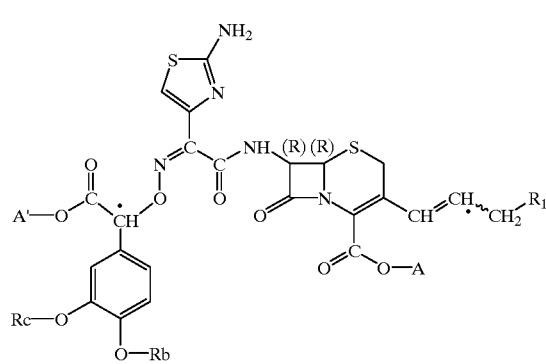

in the R or S form or in the form of an R, S mixture wherein R us selected from the group consisting of

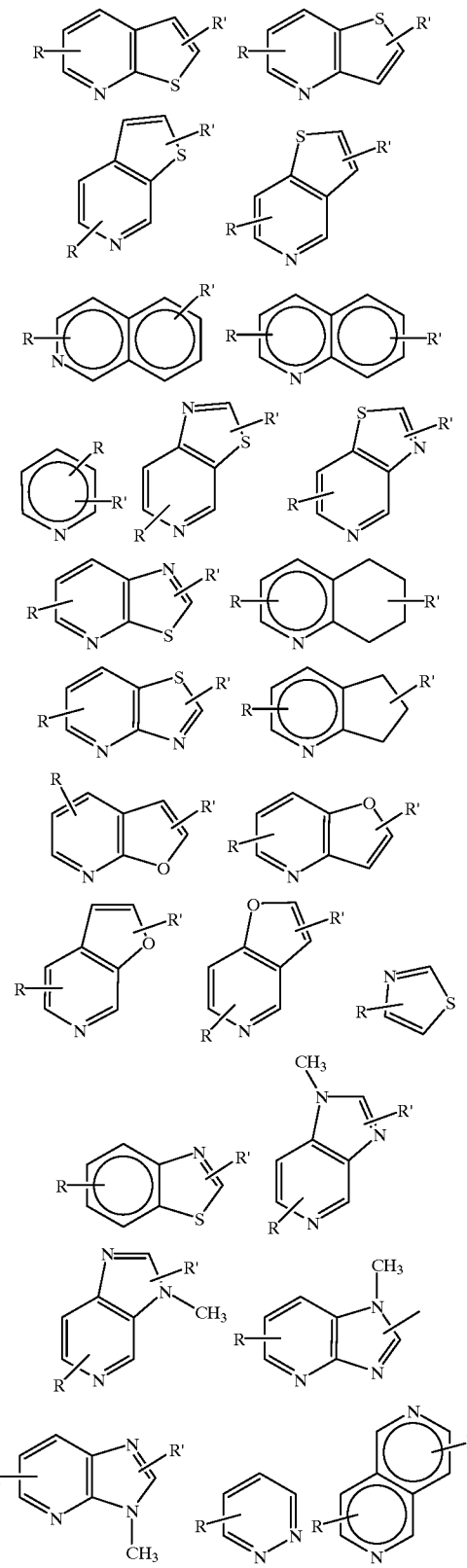

-continued

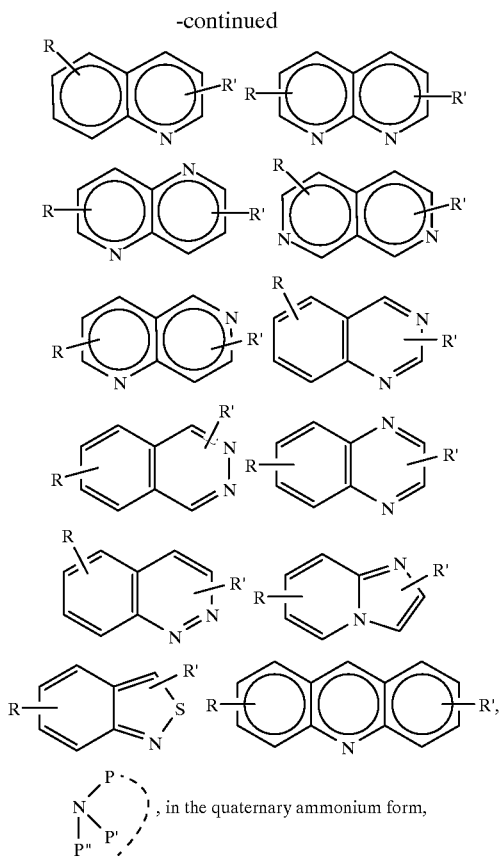

, in the quaternary ammonium form,

-continued

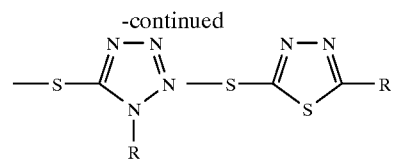

R and R' are individually selected from the group consisting of hydrogen, alkyl of 1 to 4 carbon atoms, alkoxy of 1 to 4 carbon atoms, halogen, $CO_2$—Q,

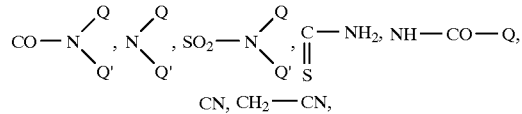

CN, $CH_2$—CN, $CH_2$—SQ, Q and Q' are individually hydrogen or alkyl of 1 to 4 carbon atoms, P, P' and P" are individually alkyl of 1 to 4 carbon atoms optionally substituted by one of the substituents R and R' the dotted line indicating that P and P' can optionally form with the nitrogen atom to which they are linked a heterocycle with 5 or 6 links, $R_b$ and $R_c$ are individually selected from the group consisting of an equivalent of an alkali metal, an alkaline earth metal, magnesium, ammonium and an amine organic base or A and A' are the remainder of an easily cleavable ester group or $CO_2A$ is $CO_2$—and the wavy line indicates that $CH_2R_1$ is in the E or Z position and their non-toxic, pharmaceutically acceptable acid addition salts having anti-bacterial activity.

1 Claim, No Drawings

CEPHALOSPORINS

PRIOR APPLICATION

This application is a division of U.S. Pat. application Ser. No. 449,243 filed May 24, 1995, now U.S. Pat. No. 5,541,318, which is a division of U.S. Pat. application Ser. No. 106,380 filed Aug. 13, 1993, now abandoned, which is a division of U.S. Pat. application Ser. No.07/987,007 filed Dec. 7, 1992, now U.S. Pat. No. 5,397,779, which is a continuation-in-part of U.S. Pat. application Ser. No. 07/715,510 filed Jun. 14, 1991, now abandoned.

STATE OF THE ART

Related prior art includes U.S. Pat. No. 4,486,586; No. 4,751,295 and No. 4,921,850, PCT application No. WO 87-03875 and European Patent applications No. 0,315,518; NO. 0,333,154 and No. 0,266,060.

OBJECTS OF THE INVENTION

It is an object of the invention to provide the novel syn isomers of the compounds of formula I and their non-toxic, pharmaceutically acceptable acid addition salts and a novel process and novel intermediates for their preparation.

It is another object of the invention to provide novel anti-bacterial compositions and a novel method of combatting bacterial infections in warm-blooded animals.

These and other objects and advantages of the invention will become obvious from the following detailed description.

THE INVENTION

The novel compounds of the invention are selected from the group consisting of the syn isomer of a compound of the formula

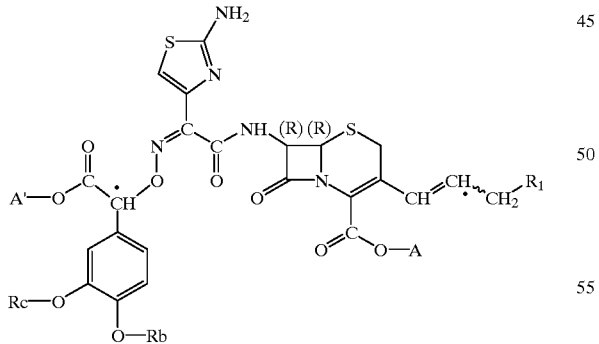

I in the R or S form or in the form of an R, S mixture wherein $R_1$ is selected from the group consisting of

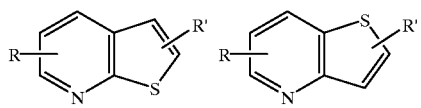

-continued

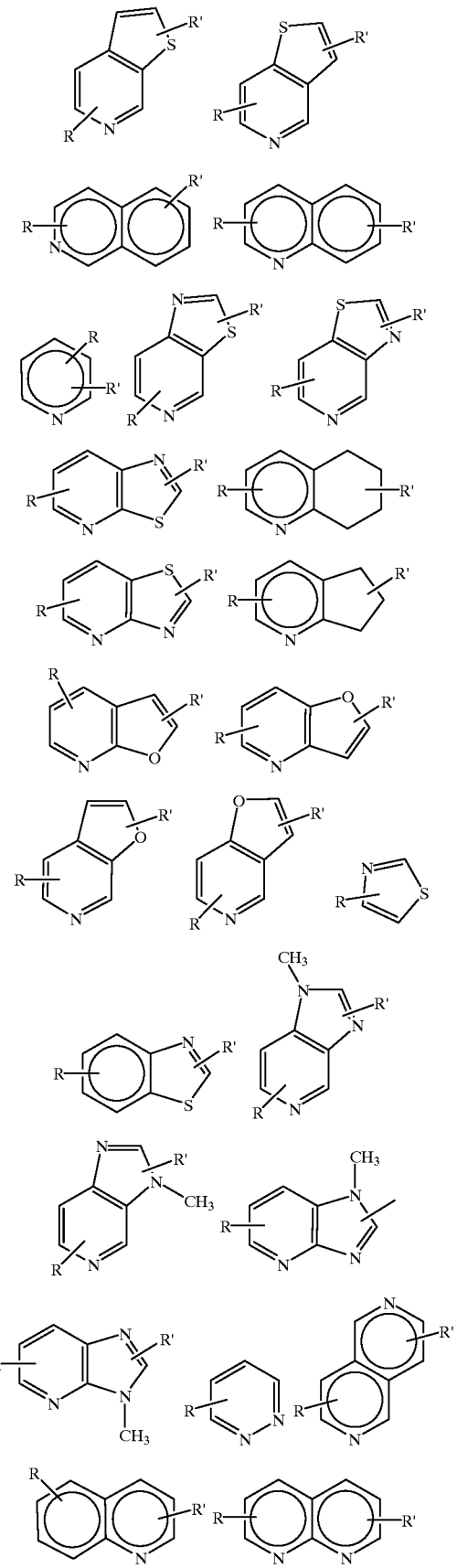

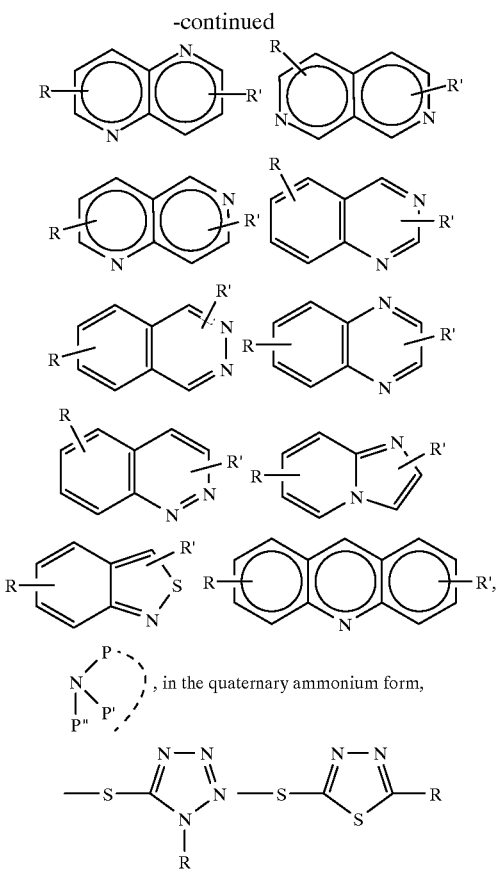

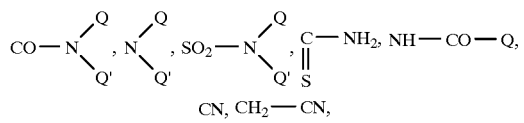

R and R' are individually selected from the group consisting of hydrogen, alkyl of 1 to 4 carbon atoms, alkoxy of 1 to 4 carbon atoms, halogen, $CO_2$—Q, $$CO-N\diagup_{Q'}^{Q},\ N\diagup_{Q'}^{Q},\ SO_2-N\diagup_{Q'}^{Q},\ \underset{S}{\overset{Q}{\underset{\|}{N-C}}}-NH_2,\ NH-CO-Q,$$

$$CN,\ CH_2-CN,$$

$CH_2$—SQ, Q and Q' are individually hydrogen or alkyl of 1 to 4 carbon atoms, P, P' and P'' are individually alkyl of 1 to 4 carbon atoms optionally substituted by one of the substituents for R and R', the dotted line indicating that P and P' can optionally form with the nitrogen atom to which they are linked a heterocycle with 5 or 6 links, $R_b$ and $R_c$ are individually hydrogen or acyl, A and A' are individually selected from the group consisting of hydrogen, an equivalent of an alkali metal, an alkaline earth metal, magnesium, ammonium and an amine organic base or A and A' are the remainder of an easily cleavable ester group or $CO_2A$ is $CO_2$—, and the wavy line indicates that $CH_2R_1$ is in the E or Z position and their non-toxic, pharmaceutically acceptable acid addition salts.

Examples of alkyl of 1 to 4 carbon atoms are methyl, ethyl, propyl, isopropyl and linear or branched butyl. When P and P' form a heterocycle with the nitrogen to which they are attached, it is preferably pyrrolidino, piperidino or morpholino.

When $R_b$ and/or $R_c$ is acyl, it may be acetyl, propionyl or benzoyl, preferably acetyl. However, $R_b$ and $R_c$ are preferably hydrogen.

Among the preferred values of A and A' are an equivalent of sodium, potassium, lithium, calcium, magnesium or ammonium. Examples of the organic bases are methylamine, propylamine, trimethylamine, diethylamine, triethylamine, N,N—dimethylethanolamine, tris [(hydroxymethyl) -amino]-methane, ethanolamine, pyridine, picoline, dicyclohexylamine, morpholine, benzylamine, procaine, lysine, arginine, histidine and N—methylglucamine.

Examples of easily cleavable ester groups of A and A' are methoxymethyl, ethoxymethyl, isopropyloxymethyl, alpha-methoxy ethyl, methyl-thiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert-butylcarbonyloxymethyl, hexadecanoyloxymethyl, propionyloxyethyl, isovaleryloxyethyl, 1-acetyloxyethyl, 1-propionyloxyethyl, 1-butyryloxyethyl, 1-tert-butylcarbonyloxyethyl, 1-acetyloxypropyl, 1-hexadecanoyloxyethyl, 1-propionyloxypropyl, 1-methoxycarbonyloxyethyl, methoxycarbonyloxymethyl, 1-acetyloxybutyl, 1-acetyloxyhexyl, 1-acetyloxyheptyl, phthalidyl, 5,6-dimethoxyphthalidyl, tert-butylcarbonylmethyl, allyl, 2-chloroallyl, methoxycarbonylmethyl, benzyl and tert-butyl.

Other ester groups for A and A' are methoxyethoxymethyl, dimethylaminoethyl, cyanomethyl, tert-butoxycarbonylmethyl, 2,2-ethylenedioxyethyl, cyanoethyl, 2,2-dimethoxyethyl, 2-chloroethoxymethyl-2-hydroxyethoxy-ethyl, 2,3-epoxypropyl, 3-dimethylamino, 2-hydroxypropyl, 2-hydroxyethyl, 2-methylaminoethoxymethyl, 2-aminoethoxymethyl, 3-methoxy-2,4-thiadiazol-5-yl, 2-tetrahydropyrannyl-1-methoxy-1-methylethyl, 2-hydroxy-1-methylethyl, isopropyl, carbamoylmethyl, chloromethyl, 2-chloroethyl, acetylmethyl, 2-methylthioethyl and thiocyanatomethyl.

Among the other esters groups for A and A' are 2-chloro-1-acetyloxyethyl, 2-bromo-1-acetyloxyethyl, 2-fluoro-1-acetyloxyethyl, 2-methoxy-1-acetyloxyethyl, 2-methyl-1-acetyloxypropyl, 1-methyl-1-acetyloxyethyl, 1-methoxyacetyloxyethyl, 1-acetylcarbonyloxyethyl, 1-hydroxyacetyloxyethyl, 1-formylcarbonyloxyethyl, 1-(2-thienyl)-carbonyloxyethyl, 1-(2-furyl)-carbonyloxyethyl, 1-(5-nitro-2-furyl)-carbonyloxyethyl, 1-(2-pyrrolyl)-carbonyloxyetlhyl, 1-propionyloxycarbonyloxy)-ethyl, 1-(propyloxycarbonyloxy)-ethyl, 1-(isopropyloxycarbonyloxy)-ethyl, 1-(methoxyethoxycarbonyloxy)-ethyl, 1-allyloxycarbonyloxy)-ethyl, isopropyloxycarbonyl-methyl, 1-[(2,3-epoxypropyl)-oxycarbonyloxy]-ethyl, 1-[(2-furyl)-methoxycarbonyloxy]-ethyl, 1-(2-fluoro-ethyl)-oxycarbonyloxyethyl, 1-(methoxycarbonyloxy)-propyl, 1-(methoxycarbonyloxy)-1-methyl-ethyl, (methoxycarbonyloxy)-chloromethyl, 1-methoxy-1-(methoxycarbonyloxy)-2-chloroethyl, 1-(methoxycarbonyloxy)-2-methoxy-ethyl, 1-(methoxycarbonyloxy)-allyl and a remainder of the formula

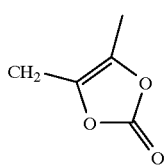

Examples of the acids for the formation of the non-toxic, pharmaceutically acceptable acid addition salts are inorganic acids such as hydrochloric acid, hydrobromic acid, hydroiodic acid, sulfuric acid, nitric acid and sulfuric acid and organic acids such as formic acid, acetic acid, propionic acid, trifluoroacetic acid, benzoic acid, tartaric acid, fumaric acid, maleic acid, methane sulfonic acid, benzene sulfonic acid and p-toluene sulfonic acid, Preferably A' is hydrogen or sodium, most preferably-hydrogen and —COOA is —COO. The expression "in the form of quaternary ammonium" means that $R_1$ is linked by the nitrogen or one of the nitrogen atoms that it contains.

Among the preferred compounds of formula I are those wherein $R_1$ is selected from the group consisting of

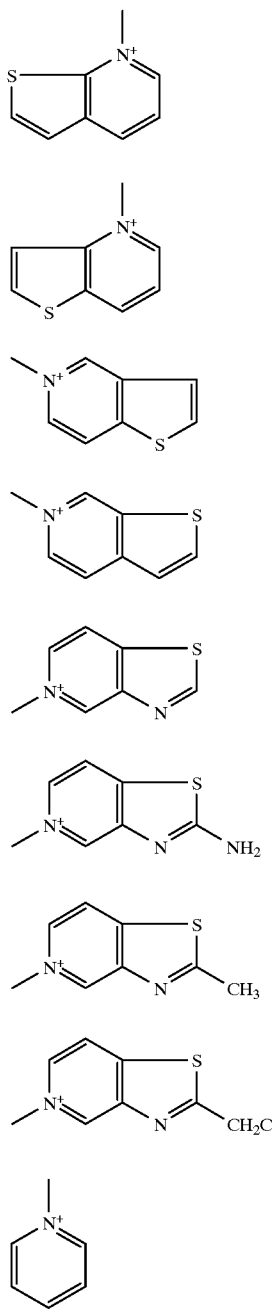

-continued

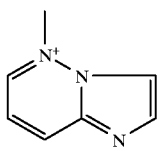

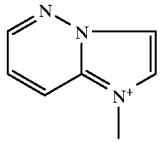

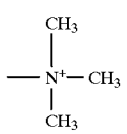

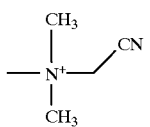

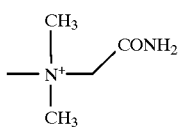

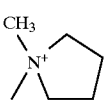

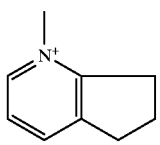

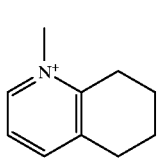

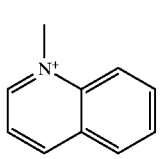

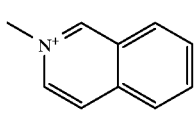

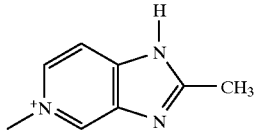

-continued

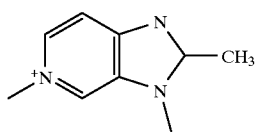

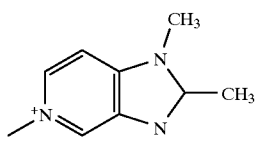

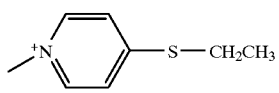

In a more preferred group consisting of formula I, $R_1$ is selected from the group consisting of

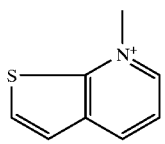

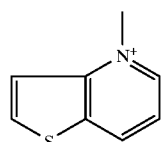

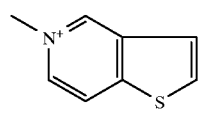

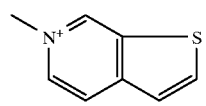

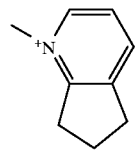

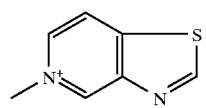

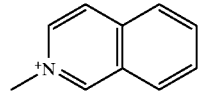

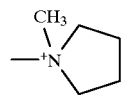

-continued

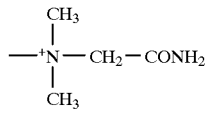

most preferably

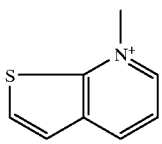

Among the specific preferred compounds of formula I are a) (6R-[3(E), 6α, 7β-(Z)]]-5-[3-[7-[[(2-amino-4-thiazolyl)-[1-(3,4-dihydroxyphenyl)-2-hydroxy-2-oxoethoxy]-imino] acetamido]-2-carboxy-8-oxo-5-thia-1-azabicyclo-[4,2,0]-oct-2-en-3-yl]-2-propenyl]-thiazolo-[4,5-c]-pyridinium in the R or S form or in the form of an R, S mixture and in the form of an internal salt or a salt with alkali metals, alkaline earth metals, magnesium, ammonia, amine organic bases, acids and its easily cleavable esters, b) [6R-[3(E), 6α, 7β-(Z)]]7-[3-[7-[[(2-amino-4-thiazolyl)-[1-(3,4-dihydroxyphenyl)-2-hydroxy-2-oxoethoxy]-imino]-acetamido]-2-carboxy -8-oxo-5-thia-1-azabicyclo-[4,2,0]-oct-2-en-3-yl]-2-propenyl]-thieno-[2,3-b]-pyridinium in the R or S form or in the form of an R, S mixture and in the form of an internal salt or a salt with alkali metals, alkaline earth metals, magnesium, ammonia, amine organic bases, acids and its easily cleavable esters and particularly in the S form, c) [6R-[3E), 6α, 7β-(Z)]]-2-[3-[7-]](2-amino-4-thiazolyl)-[1-(3,4-dihydroxyphenyl)-2-hydroxy-2-oxoethoxy]-imino]-acetamido]-2-carboxy -8-oxo-5-thia-1-azabicyclo-[4,2,0]-oct-2-en-3-yl]-2-propenyl isoquinolinium in the R or S form or in the form of an R, S mixture and in the form of an internal salt or a salt with alkali metals, alkaline earth metals, magnesium, ammonia, amine organic bases, acids and its easily cleavable esters, d) [6R-[3(E), 6α, 7β-(Z)]]-1-[3-[7-[[(2-amino-4-thiazolyl)-[1-(3,4-dihydroxyplhenyl)-2-hydroxy-2-oxoethoxy]-imino]-acetamido]-2-carboxy -8-oxo-5-thia-1-azabicyclo-[4,2,0]-oct-2-en-3-yl]-2-propenyl]-1-methyl pyrrolidinium in the R or S form-or the form of an R, S mixture and in the form of an internal salt or a salt with alkali petals, alkaline earth metals, magnesium, ammonia, amine organic bases, acids and its easily cleavable esters, e) [6R-[3(E), 6α, 7β-(Z)]]-1-[3-[7-[[(2-amino-4-thiazolyl)-[1-(3,4-dihydroxyphenyl)-2-hydroxy-2-oxoethoxy]-imino]-acetamido]-2-carboxy -8-oxo-5-thia-1-azabicyclo-[4,2,0]-oct-2-en-3-yl]-2-propenyl]-6,7-dihydro-5H—pyrindinium in the R or S form or in the form of an R, S mixture and in the form of an internal salt or a salt with alkali metals, alkaline earth metals, magnesium, ammonia, amine organic bases, acids and its easily cleavable esters and f) [6R-[3(E), 6 , 7 -(Z)]]—N—(2-amino-2-oxoethyl)-3-[7-[[(2-amino-4-thiazolyl)-[1-(3,4-dihydroxyphenyl)-2-hydroxy-2-oxethoxy]-imino]-acetamido]-2-carboxy-8-oxo-5-thia-1-azabicyclo-[4,2,0]-oct-2-en-3-yl]—N,N—dimethyl-2-propen-1-aminium in the R or S form or in the form of an R, S mixture and in the form of an internal salt or salt with alkali metals, alkaline earth metals, magnesium, ammonia, amine organic bases, acids and its easily cleavable esters.

It is understood that the products of formula I can exist either in the form indicated by formula I or in the form of products of the formula

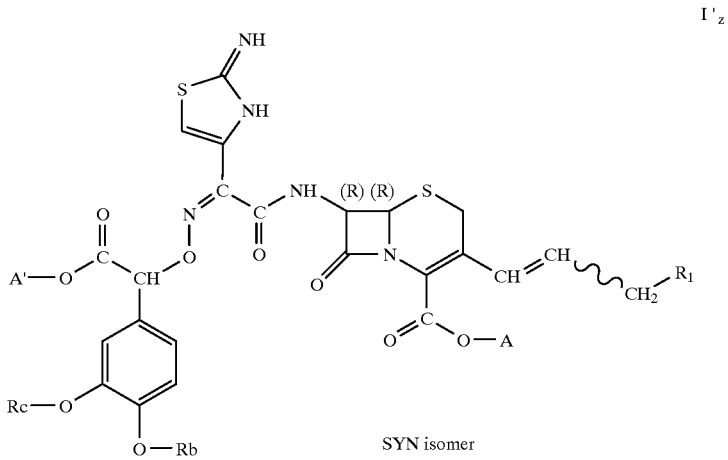

I'$_z$

SYN isomer in which A, A', $R_1$, $R_b$ and $R_c$ have the above meanings.

The novel process of the invention for the preparation of a compound of formula I comprises reacting a compound of the formula

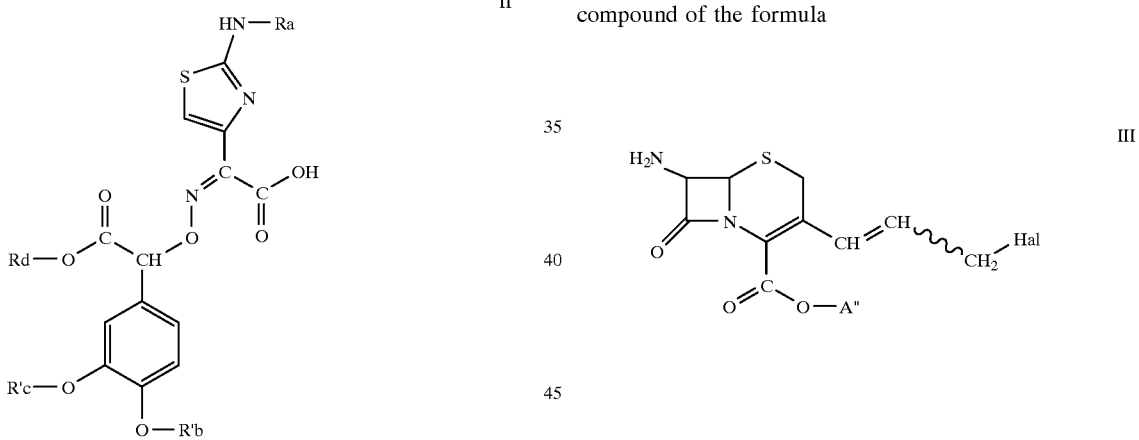

II

II racemic or optically active syn isomer or a functional derivative thereof in which $R_a$ is hydrogen or a protective group of the amino, $R_b$ and $R_c$ are individually hydrogen or a protective group of the hydroxyl, $R_d$ is hydrogen or the remainder of an easily eliminatable ester group with a compound of the formula

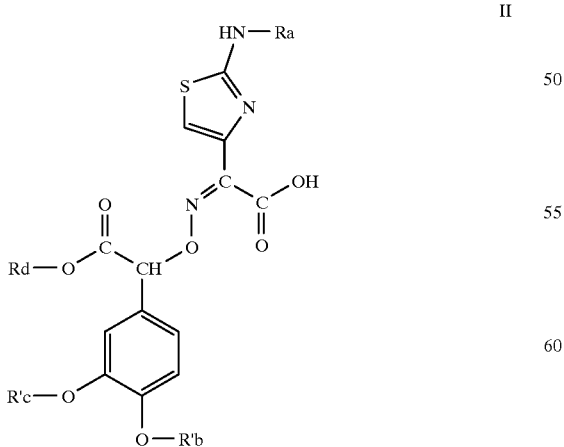

III in which Hal is halogen, A" is hydrogen or the remainder of an easily eliminatable ester group and the wavy line indicates that the $CH_2Hal$ can be found in the E or Z position to obtain a compound of the formula

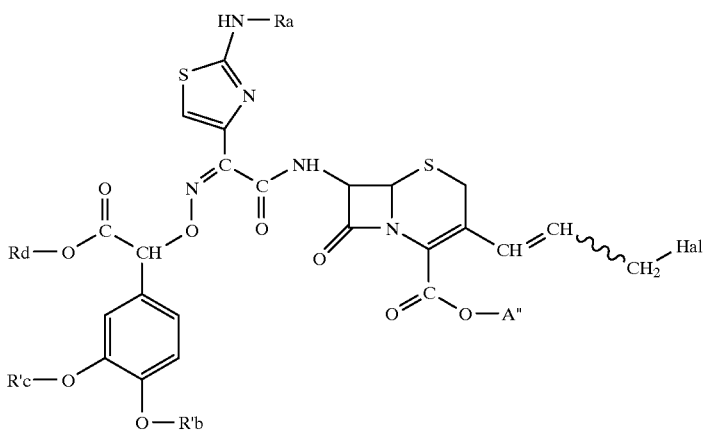

IV reacting the latter with a reagent capable of introducing $R_1$ to obtain a compound of the formula

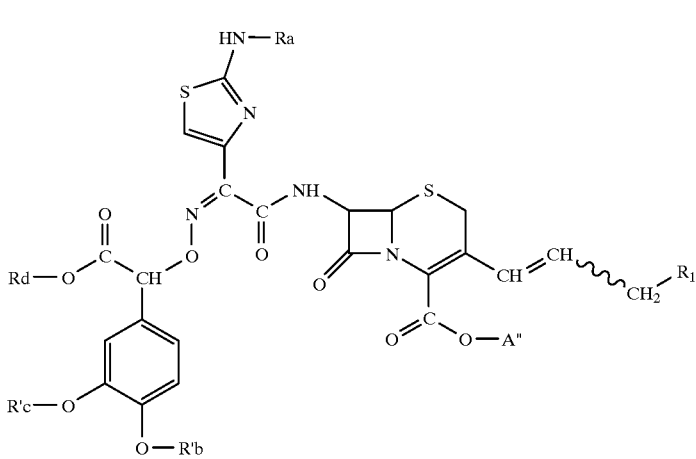

V which is optionally separated into its E or Z isomers or the Z isomers are converted into E isomers and subjecting the products of formula V, if necessary or if desired, to one or more of the following reactions in any order:

a) cleaving by hydrolysis or by the action of thiourea of all or part of the ester groups or protective groups of the amino or the hydroxyl, b) esterification or salification of the carboxylic(s) by a base, c) salification of the amino by an acid, d) separation of the products in the form of an R, S mixture into R or S.

Reagents capable of introducing $R_1$ include either when $R_1$ is a quaternary ammonium, a reagent composed of the $R_1$ itself, this not being in the form of quaternary ammonium. If one wishes to introduce a pyridinium, the operation will be done with pyridine, or when $R_1$ is

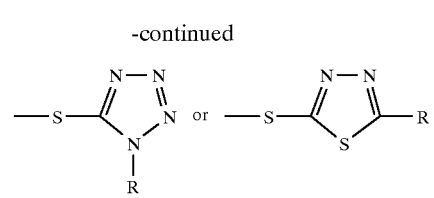

a reagent corresponding respectively to

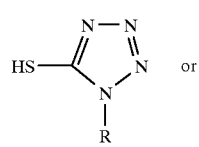

or or preferably its sodium salt

Among the preferred reagents are those of the formulae

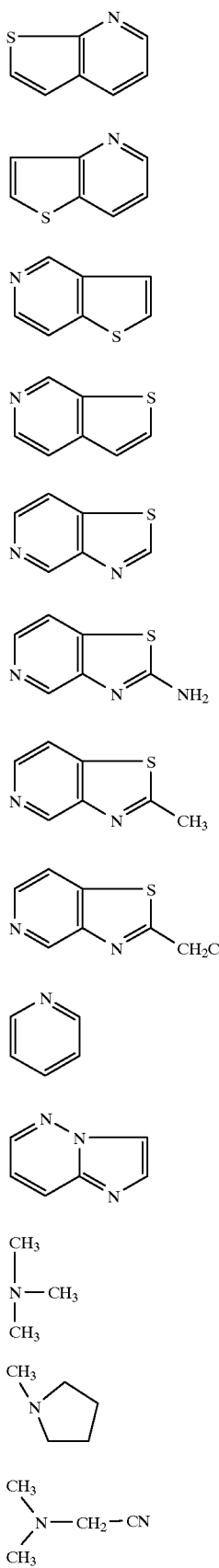
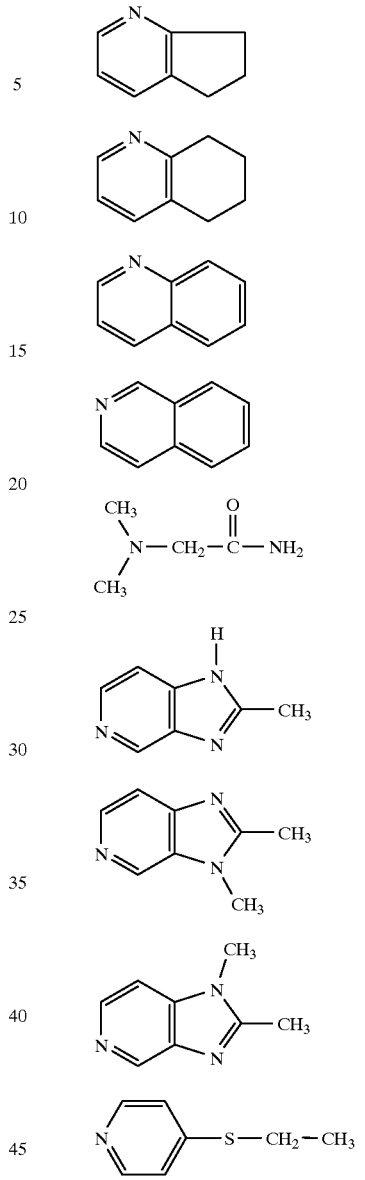

In addition to the groups mentioned above, the easily eliminable esters groups of A" and $R_d$ may be, for example, the ester formed with the following; butyl, isobutyl, tert-butyl, pentyl, hexyl, acetoxymethyl, propionyloxymethyl, butyryloxymethyl, valeryloxyinethyl, pivaloyloxymethyl, 2-acetoxyethyl, 2-propionyloxyethyl and 2-butyryloxyethyl or 2-iodoethyl, 2,2,2-trichloroethyl, vinyl, allyl, ethynyl, propynyl, benzyl, 4-methoxybenzyl, 4-nitrobenzyl, phenethyl, trityl, diphenylmethyl, 3,4-dimethyloxyphenyl, phenyl, 4-chlorophenyl, tolyl, tert-butylphenyl. Diphenylmethyl is preferred for $R_d$ and 4-methoxybenzyl or diphenylmethyl is preferred for A".

The protective group of the amino radical which is $R_a$ can be alkyl of 1 to 6 carbon atoms such as preferably, tert-butyl or tert-amyl, $R_a$ can also be aliphatic, aromatic or heterocyclic acyl or carbamoyl, The lower alkanoyl groups can be formyl, acetyl, propionyl, butyryl, isobutyryl, valerly, isovaleryl, oxalyl, succinyl, pivaloyl.

$R_a$ can also be lower alkoxy or cycloalkoxycarbonyl such as methoxycarbonyl, ethoxycarbonyl, propoxycarbonyl, 1-cyclopropylethoxycarbonyl, isopropyloxycarbonyl, butyloxycarbonyl, tert-butyloxycarbonyl, pentyloxycarbonyl, hexyloxycarbonyl, benzoyl, toluolyl, naphthoyl, phthaloyl, mesyl, phenylacetyl, phenylpropionyl and aralkoxycarbonyl such as benzyloxycarbonyl.

The acyl groups can be substituted by chlorine, bromine, iodine or fluorine such as chloroacetyl, dichloroacetyl, trichloroacetyl, bromoacetyl or trifluoroacetyl.

$R_a$ can also be lower aralkyl such as benzyl, 4-methoxybenzyl, phenetlhyl, trityl, 3,4-dimethoxybenzyl or benzhydryl or haloalkyl such as trichloroethyl or chlorobenzoyl, p-nitrobenzoyl, p-tertbutylbenzoyl, phenoxyacetyl, caprylyl, n-decanoyl, acryloxy or trichloroethoxycarbonyl.

$R_a$ can also be methylcarbamoyl, phenylcarbamoyl, naphtlhylcarbamoyl as well as the corresponding thiocarbamoyls. Trityl is preferred, The above list is not limitative and it is obvious that other amine protective groups, particularly groups known in the chemistry of peptides, can also he used.

The protective group of the hydroxyl which can be $R'_b$ and $R'_c$ can be chosen from the list below: $R'_b$ and $R'_c$ can be acyl such as formyl, acetyl, propionyl, chloroacet 1, bromoacetyl, dichloroacetyl, trichloroacetyl, trifluoroacetyl, methoxyacetyl; phenoxyacetyl, benzoyl, benzoylformyl, p-nitrobenizoyl or ethoxycarbonyl, methoxycarbonyl, propoxycarbonyl, 2,2,2-trichloroethoxycarbonyl, benzyloxycarbonyl, tert-butoxycarbonyl, 1-cyclopropylethoxycarbonyl, tetrahydropyrannyl, tetrahydrothiopyrannyl, methoxytetrahydropyrannyl, trityl, benzyl, 4-methoxybenzyl, benzyhydryl, trichloroethyl, 1-methyl-1-methoxyethyl, phthaloyl. Other acyls are butyryl, isobutyryl, valeryl, isovaleryl, oxalyl, succinyl and pivaloyl.

Also useful are phenylacetyl, phenylpropionyl, mesyl, chlorobenzoyl, p-nitrobenzoyl, p-tert-butylbenzoyl, caprylyl, acryloyl, methylcarbamoyl, phenylcarbamoyl, naphthylcarbamoyl or alkoxy alkoxymethyl such as methoxyethoxymethyl.

$OR'_b$ or $OR'_c$ can also form with the phenyl to which they are attached groups such as

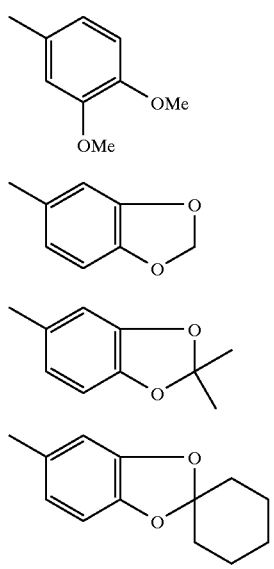

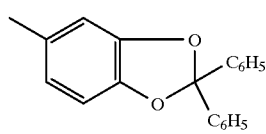

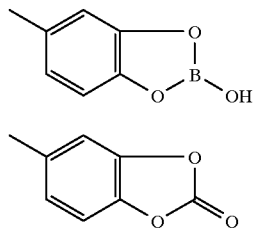

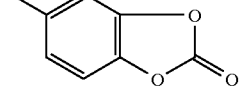

Methoxyethoxymethyl is preferred for substituents $R'_b$ and $R'_c$.

In a method for implementing the process, a functional derivative of the product of formula II is reacted which functional derivative can be a halide, a symmetrical or mixed anhydride, an amide, an azide or an activated ester. Examples of a mixed anhydride are those formed with isobutyl chloroformate and with pivaloyl chloride and the carboxylic-sulfonic mixed anhydrides formed, with p-toluene sulfonyl choride.

An example of an activated ester is the ester formed with 2,4-dinitrophenol and with hydroxybenzothiazole. An example of the halide is acid chloride or bromide. The anhydride can be formed in situ by reaction of N,N'-disubstituted carbodiimide such as N,N—dicyclohexycarbodiimide.

The acylation reaction preferably takes place in an organic solvent such as methylene chloride but other solvents such as tetrahydrofuran, chloroform or dimethylformamide may be used. When an acid halide is used, generally when an acid halide molecule is released during the reaction, the reaction is preferably carried out in the presence of a base such as sodium hydroxide, potassium hydroxide, sodium or potassium carbonate and bicarbonate, sodium acetate, triethylamine, pyridine, morpholine or N—methylmorpholine. The reaction temperature is generally lower or equal to ambient temperature.

Also a product of formula II can be reacted directly with a product of formula III in the presence of a carbodiimide such as diisopropylcarbodiimide.

The reaction of the reagents capable of introducing $R_1$ into the product of formula IV is carried out under the following conditions: When Hal is chlorine, a substitution of the chlorine by iodine in the presence of sodium iodide can be carried out in situ or separately and then the desired reagent is added, either in the presence or not of an organic solvent such as acetonitrile or tetrahydrofuran. The desired reagent can also be reacted in the presence of silver tetrafluoroborate on the product of formula IV in which Hal is chlorine.

The isomerism of the products of formula V can be different than that of the products of formula IV used at the start. In the case where the Z isomer is isolated, this isomer can be converted into the E isomer by known methods, preferably by the action of iodine.

Depending upon the values of $R_a$, $R'_b$, $R'_c$, $R_d$ and A", the products of formula V can or cannot constitute the products of formula I. The products of formula V constitute the products of formula I when $R_a$ is hydrogen, when $R'_b$ and $R'_c$ are not a protective group of the hydroxyl that one wishes to eliminate, namely when R'$_b$ and/or R'$_c$ is acyl and when R$_d$ and A" are not among the easily cleavable ester groups, one of those that one would wish to eliminate.

In other cases, the action on the product of formula V of one or more hydrolysis agents, hydrogenolysis agents or thiourea has the object of eliminating R, when it is a protective group of the amino, of eliminating the R'$_b$ and R'$_c$ when these are protective groups of the hydroxyl and/or of eliminating the R$_d$ and A" when these are among the easily cleavable esters of those that one wishes to eliminate.

However, it is of course possible to eliminate R$_a$, R'$_b$ and R'$_c$ without touching substituents R$_d$ and A" when these must be preserved. This is the case, for example, when A" is an ester group that is to be preserved such as propionyloxymethyl. The nature of the reagents brought into play in such a case is well known to one skilled in the art, For example, a description of the various elimination methods of the different protective groups will be found in French Patent Application No. 2,499,995.

Given that the preferred protective groups used are trityl for R$_a$, methoxyethoxymethyl for R'$_b$ and R'$_c$, diphenylmethyl for R$_d$ and 4-methoxybenzyl or diphenylmethyl for A", trifluoroacetic acid without a solvent or in a solvent such as anisole or a mixture of solvents such as anisole/methylene chloride is preferably used, A salt is then obtained with trifluoroacetic acid and return to the free base can be effected by the action of a base such as triethylamine carbonate.

The salification of the products can be carried out according to usual methods. Salification can be obtained by the action of a mineral base such as sodium hydroxide or potassium hydroxide, sodium or potassium carbonate or bicarbonate on a product in acid form or on a solvate, for example, the ethanolic solvate or hydrate of this acid. Mineral acid salts such as trisodium phosphate can also be used as well as organic acid salts.

Examples of organic acid salts are sodium salts of aliphatic, linear or branched, saturated or unsaturated carboxylic acids with 1 to 18 carbon atoms and preferably with 2 to 10 carbon atoms. The aliphatic chains of these acids can be interrupted by one or more heteroatoms such as oxygen or sulfur or substituted by aryl such as phenyl, thienyl, furyl, by one or more hydroxyls or by one or more halogens such as fluorine, chlorine or bromine, preferably chlorine, by one or more carboxylic or lower alkoxycarbonyl, preferably methoxycarbonyl, ethoxycarbonyl or propyloxycarbonyl, by one or more aryloxys, preferably phenoxy.

Furthermore, as organic acids, sufficiently soluble aromatic acids can be used such as substituted benzoic acids, preferably substituted by lower alkyl radicals. Examples of such organic acids are formic acid, acetic acid, butyric acid, adipic acid, isobutyric acid, n-caproic acid, isocaproic acid, chloropropionic acid, crotonic acid, phenylacetic acid, 2-thienylacetic acid, 3-thienyl-acetic acid, 4-ethylphenylacetic acid, glutaric acid, the monoethylic ester of adipic acid, hexanoic acid, heptanoic acid, decanoic acid, oleic acid, stearic acid, palmitic acid, 3-hydroxypropionic acid, 3-methoxypropionic acid, 3-methoxythiobutyric acid, 4-chlorobutyric, 4-phenylbutyric acid, 3-phenoxybutyric acid, 4-ethylbenzoic acid, 1-propylbenzoic acid. However, sodium acetate, sodium 2-ethyl hexanoate or sodium diethyl acetate are preferably used as sodium salts.

Salification can also be obtained by the action of an organic base such as triethylamine, diethylamine, trimethylamine, propylamine, N,N—dimethylethanolamine, tris((hydroxymethyl)-amino)-methane, methylamine, ethanolamine, pyridine, picoline, dicyclohexyl amine, morpholine and benzylamine or by the action of arginine, lysine, procaine, histidine, N—methyhl glucamine. This salification is preferably carried out in a solvent or a mixture of solvents such as water, ethyl ether, methanol, ethanol or acetone.

The salts are obtained in amorphous or crystallized form according to the reaction conditions employed. Crystallized salts are prepared preferably by reacting free acids with one of the salts of the aliphatic carboxylic acids mentioned above, preferably with sodium acetate. The salification of products by mineral or organic acids is carried out in the usual conditions.

The optional esterification of products is carried out under standard conditions, generally by reacting the acid of formula I or a functional derivative thereof with a derivative of the formula Z—Re in which Z is hydroxyl or halogen such as chlorine, bromine, iodine and Re is the ester group to be introduced, a non-exhaustive list of which groups is given above. In some cases, it can be advantageous to carry out an esterification on a product whose amine and/or reactive groups which are present on the oxyimino are blocked before removing the protective group of the amine and the reactive group which are present on the oxyimino.

The products of formula I comprise several asymmetrical carbons. In the cephem nucleus which comprises two asymmetrical carbons, the two carbons are in R configuration. Furthermore, the group present on the oxyimino function also has an asymmetric carbon:

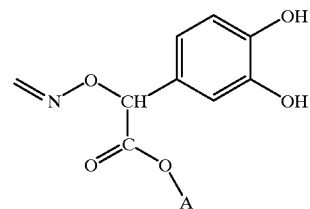

which can be in R or S form or in the form of an R, S mixture, The separation of the two diastereoisomers can be carried out by ways known to one skilled in the art, for example, by chromatography.

The novel antibiotic compositions of the invention are comprised of an antibiotically effective amount of at least one compound of formula I and its non-toxic, pharmaceutically acceptable acid addition salts and an inert pharmaceutical carrier. The compositions may be in the form of tablets, dragees, capsules, granules, suppositories, ointments, creams, gels and injectable preparations.

Examples of suitable excipients are lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can preferably be in the form of a powder to be dissolved extemporaneously in an appropriate vehicle, for example, apyrogenic sterile water.

The compositions are effective against gram (+) bacteria such as staphylococcus, streptococcus and notably on penicillin-resistant staphylococcus. Their effectiveness against gram (-) bacteria notably on coliform bacteria, klebsiella, salmonella, proteus and pseudomonas, is particularly remarkable.

These compositions are useful in the treatment of affections caused by sensitive germs and notably in that of staphylococcis such as staphylococcus septicemia, malignant staphylococcis of the face or skin, pyodermitis, septic or suppurating wounds, anthrax, phlegmons, erysipelas, acute primitive or post-influenza staphylococcis, bronchopneumonia, lung suppurations as well as in the treatment of colibacillosis and associated infections, in infections due to proteus, klebsiella and salmonella and in other affections caused by gram (−) bacteria. The compositions may also be used on disinfectants for surgical instruments.

The novel method of the invention for treating bacterial infections in warm-blooded animals, including humans, comprises administering to warm-blooded animals an antibiotically effective amount of at least one compound of formula I and its non-toxic, pharmaceutically acceptable acid addition salts. The compounds may be administered buccally, rectally, parenterally preferably intramuscularly or topically to the skin or mucous membranes. The usual daily dose is 3.33 to 53.33 mg/kg depending on the condition treated, the compound used and the method of administration. For example, the compound of Example 1 may be administered at a dose of 0.250 to 4 g per day orally or 0.500 to 1 g three times a day intra-muscularly.

The novel intermediate products of the invention are the compounds of formula IV and formula V in which $R_a$ is a protective group of the amino, formulae IV and V being as defined above.

The products of formula II are known from the literature i.e, European Patent Applications No. 0,238,061 or No. 0,266,060 or can be prepared by known methods. The products of formula III are also known from the literature, i.e. British Patent Application No. 2,134,522 or German Patent No. DE 3,512,225.

In the following examples there are described several preferred embodiments to illustrate the invention. However, it should be understood that the invention is not intended to be limited to the specific embodiments.

EXAMPLE 1

[6R-[3(E), 6α, 7β(Z)]]-7-[3-[7-[[(2-amino-thiazolyl)-[1-(3, 4-dihydroxyphenyl)-2-hydroxy-2-oxoethoxy]-imino]-acetamido]-2-carboxy -8-oxo-5-thia-1-azabicyclo-[4,2,0]-oct-2-en-3-yl]-2-propenyl]-thieno[2,3-b]-pyridinium trifluoroacetate tetrafluoroborate STEP A: [6R-[3(E), 6α, 7β(Z)]]-dibenzyl-7-[[[[1-[3,4-bis-[(2-methoxy-ethoxy)-methoxy]-phenyl]-2-(diphenylmethoxy)-2-oxoethoxy]-imino]-[2-(tribenzyl)-amino]4-thiazolyl]-acetamido]-3-(3-chloro -1-propenyl)-8-oxo-5-thia-1-azabicyclo-[4,2,0]-oct-2-ene-2-carboxylate 0.372 ml of diisopropylcarbodiimide in 1 ml of methylene chloride were added to a mixture of 1.876 g of [[[3,4-bis-(2-methoxy-ethoxy)-methoxy]-phenyl]-(diphenyl-methoxy-carbonyl)-methoxy]-imino]-[2-(triphenyl-methylamino)-4-thiazolyl] acetic acid syn isomer [described in the European Patent EP No. 238,061], 0.955 g of dibenzyl-7-amino-3-(3-chloro-1-propenyl) -8-oxo-5-thia-1-azabicyclo-[4,2,0]-oct-2-ene-2-carboxylate [described in the German Patent No. DE 3,512,225] and 200 ml of dried methylene chloride. The mixture was stirred for 45 minutes and then the solvent was evaporated off under reduced pressure. The residue was chromatographed on silica (eluant: methylene chloride 87.5—ethyl acetate 12.5) to obtain 2.1 g of a yellow product with a Rf=0.42 thin layer chromatography eluant: methylene chloride—ethyl acetate (8-2).

| Infrared Spectrum: | |
|---|---|
| =C—NH | 3402 cm$^{-1}$ |
|  | 1792 cm$^{-1}$ beta lactam |
| >=O | 1731 cm$^{-1}$ ester |
|  | 1683 cm$^{-1}$ secondary amide |
| C=C | 1594 cm$^{-1}$ |
| + | 1584 cm$^{-1}$ |
| Aromatic | 1525 cm$^{-1}$ |
| + | 1517 cm$^{-1}$ |
| Secondary amide | 1396 cm$^{-1}$ |

| Ultraviolet Spectrum: | | |
|---|---|---|
| 1) In EtOH + 1 cm$^{-3}$ CHCl$_2$ | | |
| infl | 217 nm | epsilon = 74,300 |
| infl | 238 nm | epsilon = 35,500 |
| infl | 271 nm | epsilon = 20,800 |
| infl | 296 nm | epsilon = 16,400 |
| 2) In EtOH + HCl 0.1 N | | |
| infl | 217 nm | epsilon = 76,400 |
| infl | 239 nm | epsilon = 28,800 |
| max | 283 nm | epsilon = 26,200 |
| infl | 271, 291 and 305 nm | |

STEP B: [6R-[3(E), 6α, 7β (Z)]]-7-[3-[7-[[[1-[3,4-bis-[(2-methoxy-ethoxy)-methoxy]-phenyl]-2-[(diphenyl-methoxy)-2-oxo-ethoxy]-imino]-[2-(tribenzyl)-amino]-4-thiazolyl]-acetamido]-2-[(diphenylmethoxy)-carbonyl]-8-oxo-5-thia-1-azabicyclo-[4,2,0]-oct-2-en-3-yl]-2-propenyl]-thieno-[2,3-b]-pyridinium tetrafluoroborate A mixture of 55.9 mg of silver tetrafluoroborate, 38.8 mg of thieno-[2,3-b]-pyridine and 5 ml of methylene chloride was treated with ultrasoics and then 136 mg of the product of Step A slightly diluted in methylene chloride was added. The mixture was stirred for 75 minutes and after filtering and evaporating, the residue was taken up in ether. The solid was washed 3 times with 3 ml of ether to obtain 207 mg of product which was purified by chromatography on silica (eluant: methylene chloride—methanol). The fractions were evaporated to obtain 62 mg of the desired product with a Rf=0.28 thin layer chromatography (eluant: methylene chloride—methanol (9:1).

| Ultraviolet Spectrum: | | |
|---|---|---|
| 1) In EtOH | | |
| max | 238 nm | epsilon = 368 |
| infl | 287 nm | epsilon = 168 |
| max | 300 nm | epsilon = 184 |
| 2) In EtOH, HCl 0.1 N | | |
| infl | 236 nm | epsilon = 333 |
| max | 293 nm | epsilon = 209 |

STEP C: [6R-[3(E), 6α, 7β (Z)]]-7-[3-[7-[(2-amino-4-thiazolyl)-[[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-thieno-[2,3-b]-pyridinium trifluoroacetate tetrafluoroborate The following two solutions were mixed together at 0° C.:
a) 0.180 g of the product of Step B, 4.3 ml of methylene chloride and 0.86 ml of anisole,
b) 8.6 ml of trifluoroacetic acid and 4.3 ml of methylene chloride, and the mixture was stirred for one hour at 0° C., After evaporating, the product obtained was taken up in ether and solidified. After filtering and washing with ether, 100.6 mg of product were obtained which was placed in 3.3 ml of a trifluoroacetic acid solution with 10% of anisole. The mixture was stirred for one hour at 0° C., followed by evaporating then precipitating the product in ether. After filtering and rinsing, 87.9 mg of the expected product were obtained.

EXAMPLE 2

[6R -3(E), 6α, 7β(Z)]]-7-[3-[7-[[2-amino-4-thiazolyl)-1-[3,4-dihydroxyphenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-thieno-[2,3-b]-pyridinium in the form of an internal salt A mixture of 89.4 mg of the product of Example 1, 2.84 ml of acetonitrile and 2.84 ml of a 0.1 N solution of triethylamine carbonate was eluted on an RP 18 silica column with a CH₃CN—H₂O (50—50) mixture. The useful fractions were lyophilized to obtain 50.8 mg of the expected product,

| Infrared Spectrum (Nujol): | |
| --- | --- |
| Beta lactam | 1770 cm⁻¹ |
| Other C = O's | 1675 cm⁻¹ |
| approx. | 1598 cm⁻¹ |
| Ultraviolet Spectrum in EtOH, HC 0.1 N | |
| max 240 nm | epsilon = 28,600 |
| max 290 nm | epsilon = 24,000 |

EXAMPLE 3

[6R-[3(E), 6α, 7β(Z)]]-5-[3-[7-[[(2-amino-4-thiazolyl)-1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-thiazolo-[4,5-c]-pyridinium-trifluoroacetate iodide STEP A: [6R-[3(E), 6α, 7β(Z)]]-diphenylmethyl-7-[[1-[3,4-bis-[(2-methoxy-ethoxy)-methoxy]-phenyl]-2-(diphenyl-methoxy)-2-oxoethoxy]-imino]-[2-[(tribenzyl)-amino]-4-thiazolyl]-acetamido]-3-(3-iodo-1-prolpenyl)-8-oxo--thia-1-azabicyclo-[4,2,0]-oct-2-ene-2-carboxylate A mixture of 650 mg of the product of Step A of Example 1, 19.1 ml of acetone and 216.3 mg of sodium iodide was stirred for 2 hours at ambient temperature and the solvent was evaporated off. Then, the residue was taken up in 26.5 ml of ethyl acetate and the solution was washed 3 times with 15 ml of sodium thiosulfate, then twice with 15 ml of water. After drying on magnesium sulfate, filtering, rinsing and evaporating, the residue was taken up in a methylene chloride—ethyl acetate (7-3) mixture, 5.3 g of silica were added and the mixture was stirred for 5 minutes followed by filtering and rinsing to obtain 445 mg of the expected product after evaporation (Rf=0.54 on thin layer chromatography, eluant: methylene chloride—ethyl acetate (7-3)). NMR in CDCl₃

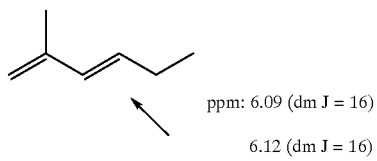

ppm: 6.09 (dm J = 16)
6.12 (dm J = 16)

STEP B: [6R-[3(E), 6α, 7β(Z)]]-5-[3-[7-[[1-[3,4-bis-[(2-methoxy-ethoxy) -methoxy]-phenyl]-2-[(diphenylmethoxy)-2-oxoethoxy]-imino]-[2-[(tribenzyl)-amino]-4-thiazolyl]-acetamido]-2-[(diphenylmethoxy)-carbonyl]-8-oxo-5-thia-1-azabicyclo-[4,2,0]-oct-2-en-3-yl]-2-propenyl]-thiazolo-[4,5-c]-pyridinium iodide A mixture of 445.2 mg of the product of Step A in the smallest possible quantity of dimethylsulfoxide and 48.2 mg of thiazolo-[4,5-c]-pyridine was stirred for 5 hours and then the solvent was eliminated under reduced pressure. The viscous residue was washed 3 times with 7 ml of ether to obtain 374.6 mg of a solid which was purified on silica (eluant: methylene chloride—methanol (92-8)) to obtain 24 mg of product having the Z isomer, 21.2 mg of an E+Z mixture and 154.3 mg of product having the E isomer (Rf=0.18 on thin layer chromatography, eluant: methylene chloride—ethanol (9-1)).

NMR (CDCl₃)

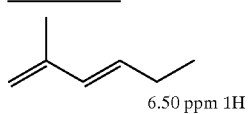

6.50 ppm 1H

STEP C: [6R-[3(E), 6α, 7β(Z)]]-5-[3-[7-[[(2-amino-4-thiazolyl)-[1-(3,4-dihydroxy-phenyl-2-hydroxy-2-oxoethoxy]-imino]-acetamido]-2-carboxy-8-oxo-5-thia-1-azabicyclo-[4,2,0]-oct-2-en-3-yl]-2-propenyl]-thiazolo-[4,5-c]-pyridinium trifluoroacetate iodide A mixture of the two following solutions was stirred for one hour: at 0° C.: a) 238.6 mg of the product of Step B, 5.7 ml of methylene chloride and 1.14 ml of anisole and b) 11.4 ml of trifluoroacetic acid in 5.7 ml of methylene chloride. The solvents were evaporated and then the product was precipitated in ether. After filtering and washing, 0.124 g of the expected product were obtained which was mixed with 4.14 ml of trifluoronacetic acid and 0.46 ml of anisole. The mixture was stirred for 40 minutes at a temperature of 0° C. After evaporating, the product was precipitated in ether. After filtering, rinsing with ether and drying, 95.8 mg of the expected product were obtained.

EXAMPLE 4

[6R-[3(E), 6α, 7β(Z)]]-5-[3-[7-[(2-amino-4-thiazolyl)-[[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-thiazolo-[4,5-c]-pyridinium in the form of an internal salt A solution of 95 mg of the product of Example 3, 3.6 ml of acetonitrile and 3.8 ml of triethylamine carbonate was passed through an RP18 silica column, The column was eluted with a mixture of acetonitrile-water (50—50) and the useful fractions were lyophilized to obtain 63.8 mg of the expected product.

| Ultraviolet Spectrum (in EtOH, HCl 0.1 N) | | |
| --- | --- | --- |
| max | 225 nm | epsilon = 38,500 |
| max | 286 nm | epsilon = 23,500 |
| infl | 274, 300 and 356 nm | |
| Infrared Spectrum (Nujol) | | |
| | | 1770 cm⁻¹ Beta lactam |
| | | 1676 cm⁻¹ complex |
| Aromatic region | | 1626 cm⁻¹ |
| coo ⊖ | | 1596 cm⁻¹ |
| Secondary amide | | 1536 cm⁻¹ |

EXAMPLE 5

[6R-[3(E), 6α, 7β(Z)]]-4-[3-[[[(2-amino-4-thiazolyl)-[1-(3,4-dihydroxyphenyl)-2-hydroxy-2-oxoethoxy]-imino]- acetamido]-2-carboxy -8-oxo-5-thia-1-azabicyclo-[4,2,0]-oct-2-en-3-yl]-2(E)-propenyl]-thieno-[3,2-b]-pyridinium trifluoroacetate tetrafluoroborate STEP A: 6R-[3(E), 6α, 7β(Z)]]-4-[3-[7-[[3,4-bis-[(2-methoxyethoxy)-methoxy]-phenyl]-2-[(diphenyl-methoxy)-2-oxoethoxy]-imino]-2-(triphenylmethyl)-amino]-4-thiazolyl]-acetamido]-2-[(diphenylmethoxy)-carbonyl-8-oxo-5-thia-1-azabicyclo-[4,2,0]-oct -2-en-3-yl]-2(E)-propenyl]-thieno-[3,2-b]-pyridinium tetrafluoroborate Using the procedure of Step B of Example 1, 1.2 g of the product of Step A of Example 1, 346 mg of silvere fluoroborate in 44ml of methylene chloride and 0.24 ml of thieno-[3,2-b]-pyridine were reacted to obtain after chromatography on silica (eluant: methylene chloride—methanol 92-8 then 96-4) 337 mg of the expected product.

NMR Spectrum (CDCl$_3$ 300 Hz)

| | |
|---|---|
| —CH=<u>CH</u>—CH$_2$— | 6.23(dm, J=16)delta E |
| —CH=CH—<u>CH</u>$_2$— | 5.44(m) |
| the CH's of the thienyl | 7.67(d, resolved)8.25(d, resolved) |
| the CH's of the pyridine | 7.76(m), 8.74(d, resolved), 8.93 (d, resolved) |

STEP B: [6R-[3(E), 6α, 7β(Z)]]-7-[3-[[[(2-amino-4-thiazolyl)-[1-(3,4-dihydroxyphenyl)-2-hydroxy-2-oxoethoxy]-imino]-acetamido]-2-carboxy-8-oxo-5-thia-1-azabicyclo-[4,2,0]-oct-2-en-3-yl]-2(E) propenyl]-thieno-[3,2-b]-pyridinium trifluoroacetate tetrafluoroborate Using the procedure of Step C of Example 1, 316.1 mg of the product of Step A, 1.51 ml of anisole in 7.5 ml of methylene chloride and 13.7 ml of trifluoroacetic acid in 7.5 ml of methylene chloride were reacted to obtain 183 mg of product to which another 6.3 ml of trifluoroacetic acid with 10% anisole were added. The mixture was stirred for 1 hour at 0° C. and the solvent was evaporated off. The residue was taken up in ether and the preciptate was filtered, washed with ether and dried under reduced pressure to obtain 124.1 mg of the expected product.

NMR (DMSO)

| | |
|---|---|
| =N—O—$\overset{\alpha}{\underset{}{CH}}$—CO$_2$H | 5.33 (s) |
| —CH—S<br>N | 5.15 (d) |
| S—CH$_2$— | 3.49 (m) partially masked |
| —CH=<u>CH</u>—CH$_2$ | 6.33 (dt, J = 5 and 8) delta E |
| —H=CH—CH$_2$ | |
| H$_7$<br>N$^\oplus$—CH$_2$<br>phenyl | 5.72 (m) |
| H$_5$ thiazole<br>mobile H | 6.57 to 7.07 |
| H$_6$', H$_3$', H$_2$', H$_7$', H$_5$' of thienopyridine | 8.04 to 9.36 |

EXAMPLE 6

[6R-[3(E) 6α, 7β(Z)]]-4- [3-[[[(2-amino-4-thiazolyl)-[1-(3,4-dihydroxyphenyl)-2-hydroxy-2-oxoethoxy]-imino]-acetamido]-2-carboxy-8-oxo-5-thia-1-azabicyclo-[4,2,0]-oct-2-en-3-yl]-2(E)-propenyl]-thieno-[3,2-b]-pyridinium trifluoroacetate tetrafluoroborate STEP A: [6R-[3(E), 6α, 7β(Z)]]-diphenylmethyl-7-[[1-[3,4-bis[(2-methoxy-ethoxy)-methoxy]-phenyl]-2-(diphenyl-methoxy) -2-oxoethoxy]-imino]-[2-[(tribenzyl)-amino]-4-thiazolyl]-acetamido]-3-(3-iodo-1-propenyl)-8-oxo-5-thia-1-azabicyclo-[4,2,0]-oct-2-en-2-carboxylate Using the procedure of Step A of Example 3, 3 g of the chlorinated product of Step A of Example 1 in 100 ml of acetone and 1.0 g of sodium iodide were reacted to obtain 3.3 g of iodinated derivative identical to that obtained in Example 3 which was used as is in the following step.

STEP B: [6R-[3(E), 6α, 7β(Z)]]-4-[3-[7-[[1-[3,4-bis-[(2-methoxy-ethoxy)-methoxy]-phenyl]-2-[(diphenylmethoxy)-2-oxo-ethoxy]-imino]-[2-[(tribenzyl)-amino]-4-thiazolyl]-acetamido]-2-[(diphenylmethoxy)-carbonyl]-8-oxo-5-thia-1-azabicyclo-[4,2,0]-oct-2-en-3-yl]-2-propenyl]-thieno-[3,2-b]-pyridinium iodide Using the procedure of Step B of Example 3, 3.3 g of the iodinated derivative of Step A, 1.5 ml of thieno-[2,3-b]-pyridine and replacing the dimethylsulfoxide with methylene chloride were reacted to obtain 1.08 g of the expected product.

NMR Spectrum:

| | |
|---|---|
| —CH=CH—<u>CH</u>$_2$—N$^+$ | 5.69 to 5.84 (m) 3H (+H$_7$) |
| —CH=<u>CH</u>—CH$_2$—N$^+$ | 6.33 (dt), 6.46 (dt) |
| H of thienopyridine | 7.83 to 9.72 |

STEP C: [6R-[3(E), 6α, 7β(Z)]]-4-[3-[[(2-amino-4-thiazolyl)-[[1-(3,4-dihydroxyphenyl)-2-hydroxy-2-oxoethoxy]-imino]-acetamido]-2-carboxy-8-oxo-5-thia-1-azabicyclo-[4,2,0-oct-2-en-3-yl]-2-(E)-propenyl]-thieno-[3,2-b]-pyridinium trifluoroacetate tetrafluoroacetate The following two solutions were mixed together at 0° C. and stirred for one hour: a) 55 ml of trifluoroacetic acid, 5.5 ml of anisole and 25 ml of methylene chloride and b) 1.19 g of the product of Step B in 20 ml of methylene chloride and the synthesis was continued as in Step C of Example 3 to obtain 0.62 g of the expected product.

NMR Spectrum (DMSO 400 Hz)

| | |
|---|---|
| =N—O—$\overset{\alpha}{\underset{}{CH}}$—CO$_2$H | 5.33 (s) |
| —CH—S<br>N | 5.15 (d, resolved) |
| S—CH$_2$— | 3.49 (m) partially masked |
| —CH=<u>CH</u>—CH$_2$ | 6.33 (dt, J = 16 and 8) delta E |
| —H=<u>CH</u>—CH$_2$<br>and | 5.72 (m) |
| —CH=CH—CH$_2$<br>phenyl | |
| H$_5$ thiazole<br>mobile H | 6.57 to 7.01 |
| H'$_6$, H'$_3$, H'$_2$, H'$_7$, H'$_5$ of thienopyridine | 8.04 to 9.36 |

EXAMPLE 7

[6R- [3(E), 6α, 7β(Z)]]-1-[3-[7-[[[(2-amino-4-thiazolyl)-[1-(3,4-dihydroxy-phenyl)-2-hydroxy-2-oxoethoxy]-imino]-acetamido -2-carboxy-8-oxo-5-thia-1-azabicyclo-[4,2,0]-oct-2-en-3-yl]-2-propenyl]-pyridinium trifluoroacetate hydroiodide STEP A: [6R-[3(E), 6α, 7β(Z)]]1-[3-[7-[[1-[3,4-bis-[(2-methoxy-ethoxy)-methoxy]-phenyl]-2-[(diphenylmethoxy)-2-oxo-ethoxy]-imino]-[2-[(tribenzyl)-amino]-4-thiazolyl]-acetamido]-2-[(diphenylmethoxy)-carbonyl]-8-oxo-5-thia-1-azabicyclo-[4,2,0]-oct-2-en-3-yl]-2-propenyl]-pyridinium iodide Using the procedure of Step B of Example 6, 1.47 g of the ioinated derivative of Step A of Example 3 and 480 micro liters of pyridine were reacted to obtain 0.640 g of the expected product.

| NMR (CDCl₃ 400 MHz): | |
|---|---|
| —CH=CH—$\underline{CH_2}$—N⊕ | 5.15 to 5.50 |
| —CH=$\underline{CH}$—CH₂—N⊕ | 6.5(dt, resolved)delta E |
| H₂ and H₆ of pyridine | 9.10(m) |
| H₃ and H₅ of pyridine | 7.87(m) |
| H₄ of pyridine | 8.27(t, resolved) |

STEP B: [6R-[3(E), 6α, 7β(Z)]]-1-[3-[7-[[(2-amino-4-thiazolyl) -[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-pyridinium trifluoroacetate hydroiodide Using the procedure of Step C of Example 6, 0.638 g of the derivative of Step A were reacted to obtain 0.314 g of the expected product.

| NMR Spectrum: | |
|---|---|
| =N—O—$\overset{\alpha}{\underline{CH}}$—CO₂H | 5.32 (s) |
| H₆ | 5.14 (d) and 5.17 (d) |
| H₇ | 5.77 (m) |
| H₅ thiazole | 6.87 (sl) |
| C—$\underline{NH}$—CH | 9.55 (d) and 9.62 (d) |
| phenyl | 6.65 to 6.80 |
| —CH=$\underline{CH}$—CH₂ | 7.01 (d, resolved) |
| —CH=$\underline{CH}$—CH₂ | 6.30 (dt) delta E |
| —CH=CH—$\underline{CH_2}$ | approx. 5.41 |
| H in position 2 and 6 of pyridine | 9.05 (d) |
| H in position 3 and 5 of pyridine approx. | 813 (d) |
| H in position 4 of pyridine | 8.64 (t) |

EXAMPLE 8

[6R-[3(E), 6α, 7β(Z)]]-6-[3-[7-[[(2-amino-4-thiazolyl) -[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3yl]-2-propenyl]-thieno-[2,3-c]-pyridinium trifluoroacetate hydroiodide STEP A: [6R-[3(E) , 6α, 7β(Z)]]-6-[3-[7-[[1-(3,4-bis-[(2-methoxy-ethoxy)-methoxy]-phenyl]-2-[(diphenylmethoxy)-2-oxo-ethoxy]-imino]-[2-[(tribenzyl)-amino]-4-thiazolyl]-acetamido]-2-[(diphenylmethoxy)-carbonyl]-8-oxo-5-thia-1-azabicyclo-[4,2,0]-oct-2-en-3-yl]-2-propenyl]-thieno-[2,3-c]-pyridinium-iodide Using the procedure of Step B of Example 6, 2.08 g of the iodinated derivative of Step A of Example 3 and 1 g of thieno-[2,3-c]-pyridine were reacted to obtain 0.98 g of the expected product.

| NMR Spectrum: | 1) In EtOH: | |
|---|---|---|
| Infl. | 220 nm | epsilon = 87,500 |
| max. | 239 nm | epsilon = 57,000 |
| Infl. | 274 nm | epsilon = 25,500 |
| max. | 306 nm | epsilon = 27,000 |
| 1) In EtOH/HCl 0.1 N: | | |
| Infl. | 220 nm | epsilon = 87,800 |
| Infl. | 236 nm | epsilon = 53,600 |
| max. | 284 nm | epsilon = 32,600 |
| max. | 293 nm | epsilon = 32,500 |
| Infl. | 320 nm | epsilon = 24,000 |

STEP B: 6R[3-(E), 6α, 7β(Z)]]-6-[3-[7-[[2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-thieno-[2,3-c]-pyridinium trifluoroacetate hydroiodide Using the procedure of Step C of Example 6, 0.966 g of the iodinated derivative of Step A were reacted to obtain 0.487 g of the expected product.

| NMR Spectrum: | |
|---|---|
| =N—O—$\overset{\alpha}{\underline{CH}}$—CO₂H | 5.32 (s) |
| H₇ | 5.78 (m) |
| H₅ thiazole | 6.86 (sl) |
| phenyl | 6.65 to 6.80 |
| H₆, H₇ thienopyridine | 7.94 (d), 8.81 (d) |
| H₄, H₅ thienopyridine | 8.53 (d), 8.78 (d) |
| H₂ thienopyridine | 9.91 (s) |
| —$\underline{CH}$=CH—CH₂ | 7.08 (dl, J=15.5) |
| —CH=$\underline{CH}$—CH₂ | 6.35 E |
| —CH—CH—$\underline{CH_2}$ | 5.47 (d) |

EXAMPLE 9

[6R-[3(E), 6α, 7β(Z)]]-1[3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-6,7-dihydro-5H—pyrindinium trifluoroacetate iodide STEP A: [6R-[3(E, 6α, 7β(Z)]]-5-[3-[7-[[1-[3,4-bis-[(2-methoxy-ethoxy)-methoxy]-phenyl]-2-[(diphenylmethoxy)-2-oxo-ethoxy]-imino]-[2-[(tribenzyl)-amino]-4-thiazolyl]-acetamido]-2-[(diphenylmethoxy)-carbonyl]-8-oxo-5-thia-1-azabicyclo-[4,2,0]-oct-2-en-3-yl]-2-propenyl]-6,7-dihydro-5H—pyrindinium iodide Using the procedure of Step B of Example 6, 1.33 g of the iodinated derivative of Step A of Example 3 and 0.585 ml of cyclopentyl pyridine were reacted to obtain 1.07 g of the expected product.

STEP B: [6R-[(3(E), 6α, 7β(Z)]]1-[3-[7-[[2-amino-4-thiazolyl)-[1-(3,4-dihydroxyphenyl)-2-hydroxy-2-oxoethoxy]-imino]-acetamido]-2-carboxy-8-oxo-5-thia-1-azabicyclo-[4,2,0]-oct-2-en-3-yl]-2-proppenyl]-6,7-dihydro-5H—pyrindinium trifluoroacetate iodide Using the procedure of Step C of Example 6, 1.053 g of the product of Step A were reacted to obtain the expected product.

| NMR SPECTRUM (DMSO 300 MHz) | |
|---|---|
| CH₂—N⁺ | 5.32 (m) 3H |
| O—CH—f | |
| Aromatic H's | |
| H₅ thiazole | 6.70 to 6.90 |
| —$\underline{CH}$—CH—CH₂ | |
| H₆ | 5.16 (d, resolved) |
| H₇ | 5.77 (m, d, resolved after exchange) |

-continued

| NMR SPECTRUM (DMSO 300 MHz) | |
|---|---|
| —S—CH$_2$ | 3.4 to 3.8 (m) |
| —CH=CH—CH$_2$ | 6.23 (d, t) delta E |
| H of cyclopentyl | 2.23–3.15–3.8 |
| H of pyridine | 7.2 (m), 8.42 (d), 8.76 (d) |
| Mobile H | 9.01 to 9.62 |
| —CH—CH—CH$_2$ | 5.47 (d) |

EXAMPLE 10

[6R-[3(E), 6α, 7β(Z)]]-2-amino-5-[3-[7-[(2-amino-4-thiazolyl)-[[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-thiazolo-[4,5-c]-pyridinium trifluoroacetate iodide STEP A: [6R-[3(E), 6α, 7β(Z)]]-2-amino-5-[3-[7-[[1-[3,4-bis-[(2-methoxy-ethoxy)-methoxy]-phenyl]-2-[(diphenylmethoxy)-2-oxo-ethoxy]-imino]-2-[(tribenzyl)-amino]-4-thiazolyl]-acetamido]-2-[(diphenylmethoxy)-carbonyl]-8-oxo-5-thia-1-azabicyclo-[4,2,0]-oct-2-en-3-yl]-2-propenyl]-thiazolo-[4,5-]-pyridinium iodide Using the procedure of Step B of Example 6, the iodinated derivative of Step A of Example 3, prepared from 272 mg of the chlorinated derivative and 90 mg of sodium iodide and 30 mg of amino thiazolo pyridine were reacted to obtain 42 mg of expected product.

STEP B: [6R-[3(E), 6α, 7β(Z)]]-2-amino-5-[3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0-oct-2-en-3-yl]-2-propenyl]-thiazolo-[4,5,-c]-pyridinium trifluoroacetate iodide.

Using the procedure of Step C of Example 3, 130 mg of the product of Step A were reacted to obtain 11.5 mg of the expected product.

| NMR Spectrum (DMSO 400 MHz) | |
|---|---|
| H$_5$ thiazole ethylenic aromatics | 6.64 to 7.41 |
| H$_6$ N$^\oplus$ —CH$_2$—CH— O—CH— | 5.05 to 5.35 |
| H$_7$ | 5.67 (m), 5.76 (m) |
| —CH=CH—CH$_2$— | 6.29 |
| H$_6$, H$_7$ of thiazolo pyridine | 8.42 (d), 8.49 (d) |
| H$_2$ of thiazolo pyridine | 8.99 (sl) |
| | 8.67 |
| mobile protons | 9 (m) |
| | 9.54 (m) |
| | 10.15 |

EXAMPLE 11

[6R-[3(E), 6α, 7β(Z)]]-5-[3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-thieno-[3,2-c]-pyridinium trifluoroacetate hydroiodide STEP A: [6R-[3(E), 6α, 7β(Z)]]-p-methoxybenzyl-7-[[1-[3,4-bis-[(2-methoxyethoxy)-methoxy]-phenyl]-2-(diphenyl-methoxy)-2-oxoethoxy]-imino]-2-[(tribenzyl)-amino]-4-thiazolyl]-acetamido]-3-(3-chloro-1-propenyl)-8-oxo-5-thia-1-azabicyclo-[4,2,0]-oct-2-en-3-yl-2-carboxylate A suspension of 3.75 g of [[(3,4-bis-[(2-methoxyethoxy)-methoxy]-phenyl]-2-(diphenylmethoxy)-2-oxoethoxy]-imino]-[2-[(tribenzyl)-amino]-4-thiazolyl]-acetic acid syn isomer [described in European Patent No. 238,061] and 1.81 g of methoxybenzyl-7-amino-3-(3-chloropropenyl)-8-oxo-5-thia-1-azabicyclo-[4,2,0]-oct-2-en-2-carboxylate [prepared in European Patent No. 0,333,154] in methylene chloride was cooled to 0° C. and 0.920 g of N—(dimethylaminopropyl)—N'-ethyl carbodiimide hydrochloride were added. The solution was stirred at 0° C. for 30 minutes and the organic phase was washed with an aqueous solution of sodium chloride and dried. The solvents were eliminated and after chromatographing the residue on silica (eluant: methylene chloride—ether 85-15) and solidification in isopropyl ether, 4.546 g of the expected product were obtained.

| NMR Spectum (CDCl$_3$ 400 MHz) | |
|---|---|
| CO$_2$—CH$_2$— | 5.10 to 5.32 |
| —O—CH$_3$ | 3.80 |

STEP B: [6R-[3(E), 6α, 7β(Z)]]-p-methoxybenzyl-7-[[1-[3,4-bis-[(2-methoxy-ethoxy)-methoxy]-phenyl]-2-(diphenyl-methoxy)-2-oxoethoxy]-imino]-2-[(tribenzyl)-amino]-4-thiazolyl]-acetamido]-3-(3-iodo-1-propenyl)-8-oxo-5-thia-1-azabicyclo-[4,2,0]-oct-2-en -3-yl-2-carboxylate A mixture of the product of Step A, 10 ml of acetone and 341 mg of sodium iodide and approximately 10 mg of iodine was stirred for one hour at ambient temperature and the solvent was evaporated. The residue was taken up in 80 ml of methylene chloride and the organic phase was washed with an aqueous solution of sodium thiosulfate, then with water. After drying, the solvents were eliminated and the residue was chromatographed on silica (eluant: methylene chloride—ethyl acetate 8-2) to obtain 853 mg of the expected product.

| NMR Spectrum (CDCl$_3$ 300 MHz) | |
|---|---|
| —CH=CH—CH$_2$ aromatics | 6.9 to 7.35 |
| CH=C | |
| —CH=CH—CH$_2$ | 6.13 (d, t J = 15 and 8) delta E |
| —CH=CH—CH$_2$ | 4.0 (d) |

STEP C: [6R-[3(E), 6α, 7β(Z)]]-5-[3-[7-[[1-[3,4-bis-[2-methoxy-ethoxy)-methoxy]-phenyl]-2-[(diphenylmethoxy)-2-oxoethoxy]-imino]-[2-[(tribenzyl)-amino]-4-thiazolyl]-acetamido]-2-[(paramethoxy-benzyloxy)-carbonyl]-8-oxo-5-thia-1-azabicyclo-[4,2,0]-oct-2-en-3-yl]-2-propenyl]-thieno-[3,2-c]-pyridinium iodide 2.48 g of the iodinated derivative of Step B, were dissolved in 10 ml of methylene chloride and 1.2 g of thieno-[3,2-c]-pyridine in solution in 2 ml of methylene chloride was added. Trituration took place for 1 hour at ambient temperature and 70 ml of ether were added. The precipitate was filtered, washed with ether and chromatographed on silica (eluant: methylene chloride—methanol 95-5) to obtain 1.117 g of the expected product.

STEP D: [6R-[3(E), 6α, 7β(Z)]]-5-[3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-thieno-[3,2-c]-pyridinium trifluoroacetate hydroiodide Using the procedure of Step C of Example 6, 1.117 g of the product of Step C were reacted to obtain 0.618 g of the expected product.

| NMR Spectrum (DMSO 300 MHz) | |
|---|---|
| $=N-O-\underline{CH}-CO_2H$ with φ branch | 5.33 (s) |
| $H_6$ | 5.18 |
| $H_7$ | 5.79 (m) |
| N—$\underline{NH}$—CH | 9.56 (d), 9.64 (d) |
| —$\underline{CH}$=CH—$CH_2$ | 7.07 (d, J=15.5) delta E |
| —CH=$\underline{CH}$—$CH_2$ | 6.36 (m) |
| H of thienopyridine | 8 to 9.71 |
| aromatics and $H_5$ thiazole | 6.70 to 6.78; 6.85 (s,1) |
| mobile H's | 12.56 |

EXAMPLE 12

[6R-[(E), 6α, 7β(Z)]]-2-[3-[7-[(2-amino-4-thiazolyl)-[[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-isoquinolinium trifluoroacetate hydroiodide STEP A: [6R-[3(E), 6α, 7β(Z)]]-2-[3[7-[[1-[3,4-bis-[(2-methoxy-ethoxy)-methoxy]-phenyl]-2-[(diphenylmethoxy)-2-oxo-ethoxy]-imino]-[2-[(tribenzyl)-amino]-4-thiazolyl]-acetamido]-2-[(p-methoxybenzyl)-carbonyl]-8-oxo-5-thia-1-azabicyclo-[4,2,0]-oct-2-en-3-yl]-2-propenyl]-isoquinolinium iodide Using the procedure of Step B of Example 6, 2.48 g of iodinated derivative of Step B of Example 11 and 1.04 ml of isoquinoline were reacted to obtain 1.26 g of the expected product.

STEP B: [6R-[3(E), 6α, 7β(Z)]]-2-[3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-isoquinolinium trifluoroacetate hydroiodide Using the procedure of Step C of Example 6, 1.26 g of the product of Step A were reacted to obtain 0.673 g of the expected product.

| NMR Spectrum (DMSO 300 MHz): | |
|---|---|
| $=N-O-\underline{CH}-CO_2H$ with φ branch | 5.32 (s) |
| $H_6$ | 5.17 (m) |
| $H_7$ | 5.77 (m) |
| S—$\underline{CH_2}$ | 3.07 |
| N—$\underline{NH}$—CH | 9.54 (d), 9.62 (d) |
| —$\underline{CH}$=CH—$CH_2$ | 7.10 delta E |
| —CH=$\underline{CH}$—$CH_2$ | 6.37 (m) delta E |
| —CH=CH—$\underline{CH_2}$— | 5.53 (d) |
| H of isoquinoline | 8.9 to 10.06 |
| aromatics and $H_5$ thiazole | 6.45 to 6.37 (3H); 6.85 (s) 1H |
| mobile H's | 7.30 (2H); 9 (2H) |

EXAMPLE 13

[6R-[3(E), 6α, 7β(Z)]]-5-[3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-2-methyl-1H—imidazo-[4,5-c]-pyridinium trifluoroacetate hydroiodide STEP A: [6R-[3(E), 6α, 7β(Z)]]-5-[3-[7-[[1-[3,4-bis-[(2-methoxy-ethoxy)-methoxy]-phenyl]-2-[(diphenylmethoxy)-2-oxo-ethoxy]-imino]-[2-[(tribenzyl)-amino]-4-thiazolyl]-acetamido]-2-[(p-methoxybenzyl)-carbonyl]-8-oxo-5-thia-1-azabicyclo-[4,2,0]-oct-2-en-3-yl]-2-propenyl]-2-methyl-1H—imidazo-[4,5-c]-pyridinium iodide Using the procedure of Step B of Example 6, 1.92 g of the iodinated derivative of Step B of Example 11 and 0.29 g of 2-methyl -1H—imidazo-[4,5-c]-pyridine were reacted to obtain 1.055 g of the expected product.

STEP B: [6R-[3(E), 6α, 7β(Z)]]-5-[3-[7-[[(2-amino-4-thiazolyl) -[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-2-methyl-1H—imidazo-[4,5-c]-pyridinium trifluoroacetate hydroiodide Using the procedure of Step C of Example 6, 1.043 g of the product of Step A were reacted to obtain 0.608 g of the expected product.

| NMR Spectrum (DMSO 300 MHz): | |
|---|---|
| $=N-O-\underline{CH}-CO_2H$ with φ branch | 5.32 (s) |
| $H_6$ | 5.15 (d, resolved) |
| $H_7$ | 5.77 (m, d, resolved after exchange) |
| S—$\underline{CH_2}$ | 3.76 (d), 3.61 (masked) |
| N—$\underline{NH}$—CH | 9.55 (d), 9.63 (d) |
| —$\underline{CH}$=CH—$CH_2$ | 6.95 (d1) |
| —CH=$\underline{CH}$—$CH_2$ | 6.35 (dt) delta E |
| —CH=CH—$\underline{CH_2}$— | 5.42 (m) |
| $CH_3$ of imidazopyridine | 2.70 (s) |
| H of pyridine | 8.16 to 9.47 |
| aromatics and $H_5$ thiazole | 6.65 to 6.80 (m) 3H; 6.86 (s) 1H |
| mobile H's | 7.34 (2H); 9.05 (m) |

EXAMPLE 14

[6R-[3(E), 6α, 7β(Z)]]-3-[7-[[(2-amino-4-thiazolyl)-[1-(3,4-dihydroxy-phenyl)-2-hydroxy-2-oxoethoxy]-imino]-acetamido]-2-carboxy -8-oxo-5-thia-1-azabicyclo-[4,2,0]-oct-2-en-3-yl]—N,N,N—trimethyl -2-propen-1-aminium-trifluoroacetate iodide STEP A: [6R-[3(E), 6α, 7β(Z)]]-3-[7[[1-[3,4-bis-[(2-methoxy-ethoxy)-methoxy]-phenyl]-2-[(diphenylmethoxy)-2-oxo-ethoxy]-imino]-[2-[(tribenzyl)-amino]-4-thiazolyl]-acetamido]-2-[(p-methoxy-benzyloxy)-carbonyl]-8-oxo-5-thia-1-azabicyclo-[4,2,0]-oct-2-en -3-yl]—N,N,N—trimethyl-2-propen-1-aminium iodide 365 mg of the iodinated derivative of Step B of Example 11, 0.7 ml of tetrahydrofuran and 220 micro liters of a solution of trimethylamine in ether (2.37 M/1) were stirred for 40 minutes at ambient temperature. 20 ml of ether were added and the precipitate was separated and chromatographed on silica (eluant: methylene chloride—methanol 92-8). The residue was taken up in ether and after elimination of the solvent, 276 mg of the expected product were obtained.

| Infra-Red Spectrum: | |
|---|---|
| =C—NH | 3404 $cm^{-1}$ + associated |
| | 1791 $cm^{-1}$ (beta lactam) |
| =O | 1728 $cm^{-1}$ esters |
| | 1685 $cm^{-1}$ amide |
| | 1632 $cm^{-1}$ (shoulder) |

| | |
|---|---|
| | 1613 cm⁻¹ |
| Conjugated system | 1596 cm⁻¹ |
| + amide II | 1586 cm⁻¹ |
| + aromatic | 1525 cm⁻¹ |
| | 1517 cm⁻¹ |
| | 1496 cm⁻¹ |
| Ultra-violet Spectrum | |
| 1) In ethanol + 1 ml CH₂Cl₂ | |
| infla 219 nm | epsilon = 74,000 |
| max. 281 nm | epsilon = 23,600 |
| infl. 295 nm | epsilon = 22,100 |
| infl. 265, 276 nm | |
| 2) In ethanol HCl 0.1 n | |
| infl. 219 nm | epsilon = 75,000 |
| max. 283 nm | epsilon = 30,000 |

STEP B: [6R-[3(E), 6α, 7β(Z)]]-3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]—N,N,N—trimethyl-2-propen-1-aminium trifluoroacetate iodide 247 mg of the product of Step A and 2.5 ml of trifluoroacetic acid with 10% of anisole were stirred for 1 hour at ambient temperature and 25 ml of isopropyl ether were added. The mixture was stirred for 10 minutes and the precipitate was isolated and dried under reduced pressure at 20° C. for 24 hours to obtain 128 mg of the expected product.

| NMR Spectrum (DMSO 300 MHz): | |
|---|---|
| 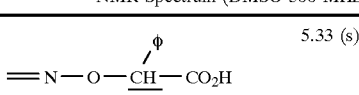 | 5.33 (s) |
| H₆ | 5.16 (d) |
| H₇ | 5.76 (d) |
| N—NH—CH | 9.08 (d) |
| —CH=CH—CH₂ | 6.07 (m) delta E |
| —CH=CH—CH₂ | 7.04 (d) |
| —CH=CH—CH₂— | 4.05 (d) |
| N—(CH₃)₃ | 2.99 (s), 3.03 (s) |
| aromatics and H₅ thiazole | 6.70 to 6.9 |

EXAMPLE 15

[6R-[3(E), 6α, 7β(Z)]]-3-[7-[[(2-amino-4-thiazolyl)[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]—N—(cyanomethyl)—N,N—dimethyl-2-propen-1-aminium]-trifluoroacetate iodide STEP A: [6R-[3(E), 6α, 7β(Z)]]-3-[7-[[1-(3,4-bis-[(2-methoxy ethoxy)-methoxy]-phenyl]-2-[(diphenylmethoxy)-2-oxoethoxy]-imino]-2-[(tribenzyl)-amino-4-thiazolyl]-acetamido]-2-[(p-methoxybenzyloxy)-carbonyl]-8-oxo-5-thia-1-azabicyclo-[4,2,0]-oct-2-en-3-yl]—N—(cyanomethyl)—N,N—dimethyl-2-propen-1-aminium]-iodide Using the procedure of Step A of Example 14, 250 mg of the iodinated derivative of Example 14 and 250 ml of a solution of dimethylamino acetonitrile in tetrahydrofuran (1-9) were reacted to obtain 172 mg of the expected product.

| NMR Spectrum (CDCl₃ 400 MHz) | |
|---|---|
| —CH=CH—CH₂ | 6.05(d, t)delta E |
| —CH=CH—CH₂ | 5.05 to 5.35 |
| CO₂—CH₂ | |
| N—CH₂—CN | 4.35 to 4.5 |
| the CH₃'s | 3.07 to 3.9 |

STEP B: [6R-[3(E) 6α, 7β(Z)]]-3-[7-[[(2-amino-4-thiazolyl)-[1-(3,4-dihydroxyphenyl)-2-hydroxy-2-oxoethoxy]-imino]-acetamido]-2-carboxy-8-oxo-5-thia-1-azabicyclo-[4,2,0]-oct-2-en-3-yl]—N—(cyanomethyl)—N,N—dimethyl-2-propen-1-aminium]-trifluoroacetate iodide Using the procedure of Step B of Example 14, 172 mg of the product of Step A were reacted to obtain 72 mg of the expected product.

| NMR Spectrum (DMSO 300 MHz): | |
|---|---|
| =N—O—CH(φ)—CO₂H | 5.33 (s) |
| H₆ | 5.20 (d) |
| H₇ | 5.82 (m) |
| N—NH—CH | 9.54 (d) |
| —CH=CH—CH₂ | 7.1 (d) |
| —CH=CH—CH₂ | 6.13 (m) |
| —CH=CH—CH₂ | 4.24 (d) |
| ⊕N—(CH₃)₂ | 3.19 (s) |
| ⊕N—CH₂—CN | 4.8 (s) |
| aromatics and H₅ thiazole | 6.65 to 6.80 and 6.87 |
| mobile H's | 7.79; 9.07 |

EXAMPLE 16

[6R-[3(E), 6α, 7β(Z)]]—N—(2-amino-2-oxoethyl)-[3-[7-[[(2-amino)-4-thiazolyl)-[1-(3,4-dihydroxyphenyl)-2-hydroxy-2-oxo-ethoxy]-imino]-acetamido]-2-carboxy-8-oxo-5-thia-1-azabicyclo-[4,2,0]-oct-2-en-3-yl]—N,N—dimethyl-2-propen-1-aminium]-trirluoroacetate iodide STEP A: [6R-[3(E), 6α, 7β(Z)]]—N—(2-amino-2-oxoethyl)-[3-[7-[[1-(3,4-bis-[(2-methoxy-ethoxy)-methoxy]-phenyl]-2-[(diphenyl-methoxy)-2-oxoethoxy]-imino]-2-[(tribenzyl)-amino]-4-thiazolyl]-acetamido]-2-[(p-methoxybenzyloxy)-carbonyl]-8-oxo-5-thia-1-azabicyclo -[4,2,0]-oct-2-en-3-yl]—N,N,-dimethyl-2-propen-1-aminium]iodide 350 mg of the iodinated derivative of Step B of Example 11 were mixed over one hour at 20° C. with 1.6 ml of acetonitrile and 27 mg of dimethylaminoacetamide. The solvents were eliminated under reduced pressure and the residue was chromatographed on silica (eluant: methylene chloride—methanol 97-3 then 92-8) to obtain 300 mg of the expected product.

| NMR Spectrum (CDCl₃ 300 MHz): | |
|---|---|
| —CH=CH—CH₂— | 6.10 delta E |
| —CH=CH—CH₂— | 4.56 |
| —CH=CH—CH₂ | |
| aromatic H's | 6.85 to 7.37 |
| NH₂ | |
| the CH₃'s | 3.24 to 3.35 |
| ⊕ N—CH₂—C | 4.23 (m) |

STEP B: [6R-[3(E), 6α, 7β(Z)]—N—(2-amino-2-oxoethyl)-[3-[7-[[(2-amino-4-thiazolyl)-[1-(3,4-dihydroxy-phenyl)-2- hydroxy-2-oxoethoxy]-imino]-acetamido]-2-carboxy-8-oxo-5-thia-1-azabicyclo-[4,2,0]-oct-2-en-3-yl]—N,N—dimethyl-2-propen-1-aminium]-trifluoroacetate iodide Using the procedure of Step B of Example 14, 285 mg of the product of Step A were reacted to obtain 152 mg of the expected product.

| NMR Spectrum (DMSO 300 MHz): | |
|---|---|
| =N—O—CH(φ)—CO$_2$H | 5.34 (s) |
| H$_6$ | 5.19 (d) |
| H$_7$ | 5.85 (m) |
| the NH's | 9.55 (d); 9.62 (d) |
| —CH=CH—CH$_2$ | 7.03 (d, J=13.5) delta E |
| —CH=CH—CH$_2$ | 6.13 (m) |
| —CH=CH—CH$_2$— | 4.27 (d) |
| $^{\oplus}$N—(CH$_3$)$_2$ | 3.19 (s) |
| $^{\oplus}$N—CH$_2$— | 4.01 (s) |
| aromatics and H$_5$ thiazole mobile H's | 6.72 to 6.8 |

EXAMPLE 17

[6R-[3(E), 6α, 7β(Z)]]-1-[3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-1-methyl-pyrrolidinium trifluoroacetate iodide STEP A: [6R-[3(E), 6α, 7β(Z)]]-[3-[7-[[1-(3,4-bis-[(2-methoxy ethoxy)-methoxy]-phenyl]-2-[(diphenylmethoxy)-2-oxo-ethoxy]-imino]-[2-[(tribenzyl)-amino]-4-thiazolyl]-acetamido]-2-[(p-methoxybenzyloxy)-carbonyl]-8-oxo-5-thia-1-azabicyclo-[4,2,0]-oct-2-en-3-yl]-2-propenyl]-1-methyl-pyrrolidinium iodide 357 mg of the iodinated derivative of Step B of Example 11 were dissolved at 20° C. in 7 ml of ether and 1.3 ml of methylene chloride and 130 microliters of methyl-pyrrolidine and 5 ml of ether were added. The mixture was stirred for 10 minutes and the precipitate was isolated and dried at 20° C. under reduced pressure to obtain 300 mg of the expected product.

STEP B: [6R-[3(E), 6α, 7β(Z)]]-1-[3-[7-[[(2-amino-4-thiazolyl-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-1-methyl pyrrolidinium trifluoroacetate iodide Using the procedure of Step B of Example 14, 290 mg of the product of Step A were reacted to obtain 150 mg of the expected product.

| NMR Spectrum (DMSO 300 MHz): | |
|---|---|
| =N—O—CH(φ)—CO$_2$H | 5.34 (s) |
| H$_6$ | 5.18 (d) |
| H$_7$ | 5.79 (m) |
| the —NH—CH's | 9.52 (d); 9.61 (d) |
| —CH=CH—CH$_2$ | 7.05 (d, J=15) delta E |
| —CH=CH—CH$_2$ | 6.17 (m) delta E |
| —CH=CH—CH$_2$— | 4.11 (d) |
| $^{\oplus}$N—CH$_3$ | 2.99 (s) |
| pyrrolidine | 2.10 (sl), 3.45 (sl) |

| NMR Spectrum (DMSO 300 MHz): | |
|---|---|
| aromatics and H$_5$ thiazole mobile H's | 6.65 to 6.85 / 9.10 |

EXAMPLE 18

[6R-[3(E), 6α, 7β(Z)]]-7-[3-[7-[[(2-amino-4-thiazolyl)-[(R) 1-(3,4-dihydroxyphenyl)-2-hydroxy-2-oxo-ethoxy]-imino]-acetamido]-2-carboxy-8-oxo-5-thia-1-azabicyclo-[4,2,0]-oct-2-en-3-yl]-2-propenyl]-thieno-[2,3-b]-pyridinium trifluoroacetate hydroiodide STEP A: [6R-[3(E), 6α, 7β(Z)]]-p-methoxybenzyl-7-[[(R)-1-(3,4-dihyroxy)-phenyl]-2-(diphenylmethoxy)-2-oxoethoxy]-imino[]2-[(tribenzyl)-amino]-4-thiazolyl]-acetamido]-3-(3-chloro-1propenyl) -8-oxo-5-thia-1-azabicyclo-[4,2,0]-oct-2-en-3-yl-2-carboxylate 1.1 g of [[(R) (3,4-dihydroxyphenyl)-(diphenyl methoxy-carbonyl)-methoxy]-imino]-[2-(tribenzyl) -4-thiazolyl]-acetic acid syn isomer [prepared for isomer S in European Patents No. 0,266,060 and 0,280,521 or in Geman Patent No. DE 3,742,457 A1] dissolved in 11.36 ml of methylene chloride were cooled to −5° C. and 403.4 mg of dicyclo-carbodiimide were added. The mixture was stirred for 40 minutes aid 668 mg of p-methoxybenzyl-7-amino-3-(3-chloro-1-propenyl)-8-oxo-5-thia-1-azabicyclo-[4,2,0]-oct-2-en-2-carboxylate hydrochloride [European Patent No. EP 0,333,154] were added. The mixture was stirred for 3 hours while allowing the temperature to return to ambient and the solvents were eliminate. The residue was chromatographed on silica (eluant: methylene chloride—ethyl acetate 9-1) to obtain 7.12 mg of the expected product.

| NMR Spectrum (CDl$_3$ 300 MHz) | |
|---|---|
| aromatics | |
| COO—CH—$_2$ | 6.74 to 7.34 |
| H$_5$ thiazole | |
| =C—CH=CH | |
| —CH=CH—CH$_2$ | 6.25 (d, J = 1) delta Z |
| —CH=CH—CH$_2$ | 3.73 (dd) |
|  | 3.92 (dd) |
| CO$_2$—CH$_2$— | 5.18 (s) |
|  | 5.24 |
| —OCH$_3$ | 3.81 (s) |

STEP B: [6R-[3(E), 6α, 7β(Z)]]-p-methoxybenzyl-7-[[(R)-1-(3,4-[(dihydroxy)-phenyl]-2-(diphenylmethoxy)-2-oxoethoxy]-imino]-[2-[(tribenzyl)-amino]-4-thiazolyl]-acetamido]-3-(3-iodo-1-propenyl) -8-oxo-5-thia-1-azabicyclo-[4,2,0]-oct-2-en-3-yl-2-carboxylate A mixture of 590 mg of the product of Step A, 11.9 ml of acetone and 216 mg of sodium iodide was stirred for 2 hours at ambient tempeature and the solvent was evaporated. The residue was taken up in 5 ml of methylene chloride and the solution was washed 3 times with 10 ml of sodium thiosulfate, then twice with 10 ml of an aqueous solution of sodium chloride. After drying and crystallizing from ether, 456.6 mg of the expected product were obtained.

| NMR Spectrum (CDCl$_3$ 400 MHz): | |
|---|---|
| =N—O—CH(φ)—CO$_2$H | 5.86 (s) |
| H$_6$ | 4.85 (d) |
| H$_7$ | 5.74 (dd) |
| S—CH$_2$ | 3.24 |
| C—NH—CH | 8.10 (d) |
| —CH=CH—CH$_2$ | 6.00 (d, J=15.5 and 17.5) delta E |
| —CH=CH—CH$_2$— | 3.82 (d), 3.98 (d) |
| —CO$_2$—CH$_2$ | 5.24 |
| —O—CH$_3$ | 3.80 (s) |
| aromatics and H$_5$ thiazole | 6.68 to 7.40 |

STEP C: [6R-[3(E), 6α, 7β(Z)]]-7-[3-[7-[[(R)-1-(3,4-bis-[(2-methoxy-ethoxy)-methoxy]-phenyl]-2-[(diphenyl-methoxy)-2-oxoethoxy]-imino]-[2-[(tribenzyl)-amino]-4-thiazolyl]-acetamido]-2-[(p-methoxybenzyloxy)-carbonyl]-8-oxo-5-thia-1-azabicyclo-[4,2,0]-oct-2-en-3-yl]-2-propenyl]-thieno-[2,3-b]-pyridinium iodide 446 mg of the iodinated derivative of Step B and 0.44 ml of thieno pyridine were stirred and triturated for 2 hours at ambient temperature. Ether was added and the solid was dried under reduced presure for 24 hours to obtain 442 mg of the expected product.

| NMR Spectrum: | |
|---|---|
| =N—O—CH— | 5.55 |
| —CH=CH—CH$_2$ | 6.30 (m) delta E |
| =N—O—CH— | 5.55 |
| CH=CH—CH$_2$ | 6.30 (m) delta E |
| —CH=CH—CH$_2$ | 5.63 to 5.69 |
| H$_7$ | |
| H of the thieno pyridine | 7.89 to 9.21 |

STEP D: [6R-[3(E), 6α, 7β(Z)]]-7-[3-[7-[[(2-amino-4-thiazolyl)-[(R)1-(3,4-dihydroxy-phenyl)-2-hydroxy-2-oxo-ethoxy]-imino]-acetamido]2-carboxy-8-oxo-5-thia-1-azabicyclo-[4,2,0]-oct-2-en-3-yl]-2-propenyl]-thieno-[2,3-b]-pyridinium trifluoroacetate hydroiodide 632 mg of the product of Step C in 6.32 ml of a solution of trifluoroacetic acid with 10% anisole were stirred for one hour at ambient temperature and the mixture was cooled to +5° C. 65 ml of isopropyl ether were added, followed by stirring for 10 minutes, filtering and drying under reduced pressure at ambient temperature for 16 hours to obtain 403 mg of the expected product.

| NMR Spectrum (DMSO 400 MHz): | |
|---|---|
| =N—O—CH(φ)—CO$_2$H | 5.31 (s) |
| H$_6$ | 5.18 (d) |
| H$_7$ | 5.77 (dd) |
| S—CH$_2$ | 3.73 (m) |
| —CH=CH—CH$_2$ | 7.15 (d, J=16) delta E |
| —CH=CH—CH$_2$ | 6.30 (d, t) |
| —CH=CH—CH$_2$ | 5.68 (d) |
| H of the thieno pyridine | 7.88 to 9.23 |
| aromatics, NH, H$_5$ thiazole | 6.70 to 7.35 (approx. 6H) |
| mobile H's | 7.31 to 9.61 |

EXAMPLE 19
[6R-[3(E), 6α, 7β(Z)]]-7-[3-[7- [[(2-amino-4-thiazolyl)-[(S)-1-(3,4-dihydroxy phenyl)-2-hydroxy-2-oxo-ethoxy]-imino]-acetamido]-2-carboxy-8-oxo-5-thia-1-azabicyclo-[4,2,0]-oct-2-en-3-yl]-2-propenyl]-thieno[-2,3-b]-pyridinium trifluoroacetate iodide STEP A: [6R-3(E), 6α, 7β(Z)]]-p-methoxybenzyl-7-[[(S)-1-(3,4-dihydroxy)-phenyl]-2-(diphenylmethoxy)-2-oxoethoxy]-imino]-2[(tribenzyl)-amino]-4-thiazolyl-acetamido]-3-(3-chloro-1-propenyl)-8-oxo-5-thia-1-azabicyclo-[4,2,0]-oct-2-en-3-yl-2-carboxylate Using the procedure of Step A of Example 18, 678 mg of [[(S) (3,4-dihydroxyphenyl)-(diphenylmethoxycarbonyl)-methoxy]-imino]-[2-(triphenyl-methylamino)-4-thiazolyl]-acetic acid syn isomer [European Patents No. 0,266,060 and 0,280,521 or in the German Patent DE 3,732,457 A1] and 412 mg of p-methoxybenzyl 7-amino-3-(3-chloro-1-propenyl)-8-oxo-5-thia-1-azabicyclo-[4,2,0]-oct-2-en-2-carboxylate hydrochloride were reacted to obtain 590 mg of the expected product.

| NMR Spectrum (CDCl$_3$ 400 MHz): | |
|---|---|
| =N—O—CH— | 5.89 (s) |
| —CH=CH—CH$_2$ | 5.81 (d, t) |
| | 6.34 (d, J = 12) |

STEP B: [6R-[3(E), 6α, 7β(Z)]]-p-methoxybenzyl-7-[[(S)-1-(3,4-dihydroxy)-phenyl]-2-(diphenylmethoxy)-2-oxoethoxy]-imino]-2-[(tribenzyl)-amino-4-thiazolyl]-acetamido]-3-(3-iodo-1-propenyl) -8-oxo-5-thia-1-azabicyclo-[4',2,0]-oct-2-en-3-yl-2-carboxylate Using the procedure of Step B of Example 18, 850 mg of the product of Step A and 335 mg of sodium iodide were reacted to obtain 595 mg of the expected product.

| Infra Red Spectrum (CHCl$_3$): | |
|---|---|
| | 3548 cm$^{-1}$ |
| OH | 3478 cm$^{-1}$ |
| NH | 3401 cm$^{-1}$ |
| | 3284 cm$^{-1}$ |
| | 1772 cm$^{-1}$ beta lactam |
| —C=O | 1725 cm$^{-1}$ ester |
| | 1684 cm$^{-1}$ amide |
| | 1614 cm$^{-1}$ |
| aromatic | 1601 cm$^{-1}$ |
| heterocycle | 1586 cm$^{-1}$ |
| amide II | 1529 cm$^{-1}$ |
| C=C | 1517 cm$^{-1}$ |
| | 1496 cm$^{-1}$ |

| Ultra Violet Spectrum: | | |
|---|---|---|
| 1) in dioxane: | | |
| infl. 224 nm | $E_1^1$ = 566 | epsilon = 69,600 |
| infl. 242 nm | $E_1^1$ = 345 | |
| infl. 275 nm | $E_1^1$ = 197 | |
| max. 282 nm | $E_1^1$ = 201 | epsilon = 24,700 |
| infl. 290 nm | $E_1^1$ = 195 | |
| max. 314 mn | $E_1^1$ = 218 | epsilon = 26,800 |
| 2) in dioxane/HCl 0.1N | | |
| max. 285 nm | $E_1^1$ = 266 | epsilon = 32,700 |
| infl. 304 nm | $E_1^1$ = 244 | epsilon = 30,000 |
| infl. 320 nm | $E_1^1$ = 188 | epsilon = 23,100 |

STEP C: [6R-[3(E), 6α, 7β(Z)]]-7-[3-[7-[[(S)-1-(3,4-bis-[(2-methoxy ethoxy)-methoxy]-phenyl]-2-[(diphenyl-methoxy)-2-oxo-ethoxy]-imino]-[2-[(tribenzyl)-amino]-4-thiazolyl]-acetamido]-2-[(p-methoxybenzyloxy)-carbonyl]-8-oxo-5-thia-1-azabicyclo-[4,2,0]-oct-2-en-3-yl]-2-propenyl]-thieno-[2,3-b]-pyridinium iodide Using the procedure of Step C of Example 18, 430 mg of the iodinated derivative of Step B and 470 mg of thieno pyridine were reacted to obtain 438 mg of the expected product.

| Infra Red Spectrum (CHCl₃): | |
|---|---|
| NH/OH region complex | |
| | 1780 cm⁻¹ beta lactam |
| —C=O | 1725 cm⁻¹ ester |
| | 1684 cm⁻¹ amide |
| | 1613 cm⁻¹ |
| | 1600 cm⁻¹ |
| aromatic | 1586 cm⁻¹ |
| heterocycle | 1575 cm⁻¹ |
| amide II | 1558 cm⁻¹ |
| + \C=C/ | 1525 cm⁻¹ |
| | 1516 cm⁻¹ |
| | 1496 cm⁻¹ |

STEP D: [6R-[3(E), 6α, 7β(Z)]]-7-[3-[7-[(2-amino-4-thiazolyl) -[(S)-1-(3,4-dihydroxy phenyl)-2-hydroxy-2-oxoethoxy]-imino-acetamido]-2-carboxy-8-oxo-5-thia-1-azabicyclo-[4,2,0]-oct-2-en-3-yl]-2-propenyl]-thieno-[2,3-b]-pyridinium trifluoroacetate iodide Using the procedure of Step D of Example 18, 400 mg of the product of Step C were reacted to obtain 275 mg of the expected product.

NMR Spectrum (DMSO 400 MHz):

| | 5.32 (s) |
|---|---|
| H₆ | 5.15 |
| H₇ | 5.79 (ddm sl after exchange) |
| CO—NH— | 9.55 (d) |
| C—NH—CH | 9.55 (d) |
| S—CH₂ | 3.51 (m) |
| —CH=CH—CH₂ | 7.13 (d, J=16) delta E |
| —CH=CH—CH₂ | 6.27 (d, t J=16 and 6) |
| —CH=CH—CH₂— | 5.67 (d, J=6) |
| H of the thieno pyridine | 7.89 to 9.55 |
| aromatics and H₅ thiazole | 6.60 to 6.87 (m) |

EXAMPLE 20

[6R-[3(E), 6α, 7β(Z)]]-5-[3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-1,2-dimethylimidazo-[4,5-c]-pyridinium trifluoroacetate hydroiodide STEP A: [6R-[3(E), 6α, 7β(Z)]]-5-[3-[7-[[1-(3,4-bis-[(2-methoxy-ethoxy)-methoxy]-phenyl]-2-[(diphenyl-methoxy)-2-oxo-ethoxy]-imino]-2-[(tribenzyl)-amino]-4-thiazolyl]-acetamido]-2-[(p-methoxybenzyloxy)-carbonyl]-8-oxo-5-thia-1-azabicyclo-[4,2,0]-oct-2-en-3-yl]-2-propenyl]-1,2-dimethylimidazo-[4,5-c]-pyridinium iodide 1.08 g of the product of Step B of Example 11 were stirred for one hour with 170 mg of 1,2-dimethyl-4-azabenzimidazole in 0.9 ml of acetonitrile and 40 ml of ether were added. The precipitate was filtered off, rinsed with ether and dried for 16 hours under reduced pressure to obtain after chromatography on silica (eluant: methylene chloride—methanol 94-6), 306 mg of the expected product.

STEP B: [3(E), 6α, 7β(Z)]]-5-[3-[7-[[2-amino-4-thiazolyl)-[1-(3,4-dihydroxyphenyl)-2-hydroxy-2-oxoethoxy]-imino]-acetyl]-amino]2-carboxy-8-oxo-5-thia-1-azabicyclo-[4,2,0]-oct-2-en-3-yl]-2-propenyl[-1,2-dimethylimidazo-[4,5-c]-pyridiniumtrifluoro-acetate hydroiodide Using the procedure of Step B of Example 14, 297 mg of the product of Step A were reacted to obtain 155 mg of expected product.

NMR Spectrum (DMSO 400 mHz):

| | 5.40 (sl) |
|---|---|
| and CH=CH—CH₂ | 5.30 (s) 3H |
| H₆ | 5.13 (d) |
| H₇ | 5.75 (m) |
| C—NH—CH | 9.63 (d), 9.65 (d) |
| —CH—CH—CH₂ | 6.98 (d, J=15.5) delta E |
| —CH=CH—CH₂ | 6.30 (d, t) |
| the CH₃'s | 2.71 (s), 3.92 (s) |
| imidazopyridine | 8.28 to 9.48 |
| aromatics and H₅ thiazole | 6.66 to 6.85 |
| mobile H's | 9.00 to 9.08 |

EXAMPLE 21

[6R-[3(E), 6α, 7β(Z)]]-5-[3-[7-[[(2-amino-4-thiazolyl)-[1-(3,4-dihydroxy phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-2,3-dimethylimidazo-[4,5-c]-pyridinium trifluoroacetate hydroiodide STEP A: [6R-[3(E), 6α, 7β(Z)]]-5-[3-[7-[[1-(3,4-bis-[(2-methoxy-ethoxy)-methoxy]-phenyl]-2-[(diphenyl-methoxy)-2-oxoethoxy]-imino]-2-[(tribenzyl)-amino]-4-thiazolyl]-acetamido]-2-(p-methoxybenzyloxy)-carbonyl]-8-oxo-5-thia-1-azabicyclo-[4,2,0]-oct-2-en-3-yl]-2-propenyl]-2,3-dimethylimidazo-4,5-c]pyridinium iodide Using the procedure of Step A of Example 20, 1.92 g of the product of Step B of Example 11 and 303 mg of 2,3-dimethyl-4-azabenzimidazole were reacted to obtain 877 mg of the expected product.

STEP B: [6R-[3-(E), 6α, 7β(Z)]]-5-[3-[7-[[(2-amino-4-thiazolyl) -[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-2,3-dimethylimidazo-[4,5-c]-pyridinium trifluoroacetate hydroiodide Using the Procedure of Step B of Example 14, 865 mg of the product of Step A were reacted to obtain 488 mg of the expected product.

NMR Spectrum (DMSO 400 mHz):

| | 5.31 (s) 3H |
|---|---|
| and CH=CH—CH₂ | 5.41 (1) |
| H₆ | 5.15 (d, resolved) |
| H₇ | 5.76 |
| C—NH—CH | 9.53 (d), 9.60 (d) |
| —CH—CH—CH₂ | (d, J=15.5) delta E |
| —CH=CH—CH₂ | 6.34 (d, t) |
| the CH₃'s | 2.75 (s), 3.94 (s) |
| imidazopyridine | 8.18 to 9.58 |

| NMR Spectrum (DMSO 400 mHz): | |
|---|---|
| aromatics and H$_5$ thiazole | 6.65 to 6.86 |
| mobile H's | 7.31 to 9.60 |

EXAMPLE 22

[6R-[3(E), 6α, 7β(Z)]]-1-[3-[7-[[(2-amino-4-thiazolyl)-[1-(3,4-didhydroxy phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-quinolinium trifluoroacetate hydroiodide STEP A: [6R-[3(E), 6α, 7β(Z)]]-1-[3-[7-[[1-(3,4-bis-[(2-methoxy ethoxy)-methoxy]-phenyl]-2-[(diphenyl-methoxy)-2-oxo-ethoxy]-imino][2-[(tribenzyl-amino]-4-thiazolyl]-acetamido]-2-[(p-methoxybenzyloxy)-carbonyl]-8-oxo-5-thia-1-azabicyclo-[4,2,0]-oct-2-en-3-yl]-2-propenyl]-quinolinium iodide Using the procedure of Step B of Example 6, 2.50 g of the iodinated derivative of Step B of Example 11 and 0.63 g of quinoline were reacted to obtain 2.40 g of the expected product which was purified by chromatography on silica (eluant: methylene chloride—methanol 95-5).

STEP B: [6R-[3(E), 6α, 7β(Z)]]-1-[3-[7-[[(2-amino-4-thiazolyl)-[1-(3,4-dihydroxy phenyl)-2-hydroxy-2-oxoethoxy]-imino]-acetamido]-2-carboxy-8-oxo-5-thia-1-azabicyclo-[4,2,0]-oct-2-en -3-yl]-2-propenyl]-quinolinium trifluoroacetate hydroiodide Using the procedure of Step B of Example 14, 1.65 g of the product of Step A were reacted to obtain 0.94 g of the expected product.

| NMR Spectrum (DMSO 400 mHz): | |
|---|---|
| =N—O—C<u>H</u>—CO$_2$H with φ | 5.31 (s) |
| H$_6$ | 5.14 (d) |
| H$_7$ | 5.75 (m) |
| C—N<u>H</u>—CH | 9.48 (d), 9.52 (d) |
| —C<u>H</u>=CH—CH$_2$ | 6.97 (d, J=15) delta E |
| —CH=CH—C<u>H</u>$_2$ | 5.89 (m) |
| H of the quinoline | 8.07 to 9.59 |
| aromatics and H$_5$ thiazole | 6.64 to 6.77; 6.85 (s) |
| mobile H's | 9.03 to 9.52 |

EXAMPLE 23

6R-[3(E), 6α, 7β(Z)]]-1-[3-[7-[[(2-amino-4-thiazolyl)-[1-(3,4-dihydroxy-phenyl)-2-hydroxy-2-oxoethoxy]-imino]-acetamido -2-carboxy-8-oxo-5-thia-1-azabicyclo-[4,2,0]-oct-2-en-3-yl]-2-propenyl]-4-ethylthio pyridinium trifluoroacetate hydroiodide STEP A: [6R-[3(E), 6α, 7β(Z)]]-1-[3-[7-[[1-(3,4-bis-[(2-methoxy-ethoxy)-methoxy]-phenyl]-2-[(diphenyl-methoxy)-2-oxoethoxy]-imino]-[2-[(tribenzyl)-amino]-4-thiazolyl]-acetamido]-2-[(p-methoxybenzyloxy)-carbonyl]-8-oxo-5-thia-1-azabicyclo-[4,2,0]-oct-2-en-3-yl]-2-propenyl]-4-ethylthio pyridinium iodide Using the procedure of Step B of Example 6, 2.50 g of the iodinated derivative of Step B of Example 11 and 1 ml of 4-ethylthio pyridine were reacted to obtain 2.45 g of the expected product which was purified by chromatography on silica (eluant: methylene chloride—methanol 95-5).

STEP B: [6R-[3(E), 6α, 7β(Z)]]-1-[3-[7-[[(2-amino-4-thiazolyl)-[1-(3,4-dihydroxy-phenyl)-2-hydroxy-2-oxoethoxy]-imino]-acetamido]-2-carboxy-8-oxo-5-thia-1-azabicyclo-[4,2,0]-oct-2-en-3-yl]-2-propenyl]-4-ethylthiopyridinium trifluoroacetate hydroiodide Using the procedure of Step B of Example 14, 1.54 g of the product of Step A were reacted to obtain 0.807 g of the expected product.

| NMR Spectrum (DMSO 400 mHz): | |
|---|---|
| 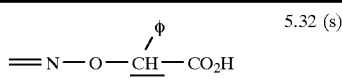 | 5.32 (s) |
| H$_6$ | 5.16 |
| H$_7$ | 5.77 (m) |
| C—N<u>H</u>—CH | 9.47 (d) |
| —C<u>H</u>=CH—CH$_2$ | 6.98 (d, J=16) delta E |
| —CH=C<u>H</u>—CH$_2$ | 6.26 (d, t) |
| H of the pyridine | 7.97 to 8.69 |
| aromatics and H$_5$ thiazole | 6.67 to 6.78; 6.87 (s) |
| mobile H's | 9.04 to 13.80 |

EXAMPLE 24: the internal salt of [6R-[3(E), 6-α, 7-β(Z)]]7-[3-[7-[[(2-amino 4-thiazolyl) [carboxy (3,4-dihydroxy phenyl) methoxy]imino]acetamido] 2-carboxy 8-oxo 5-thia 1-azabicyclo[4,2,0]oct-2-en-3-yl] 2-propenyl] furo[2,3-b]pyridinium (R) or (S) or an (R+S) mixture, Stage A: p-methoxy benzyl [6R-[3(E), 6alpha, 7beta(Z)]] 7-[[[(diphenylmethoxy carbonyl) [3,4-bis[(2-methoxy ethoxy) methoxy] phenyl] methoxy] imino] [2-[(triphenylmethyl) amino] 4-thiazolyl] acetyl] amino] 3-(3-chloro 1-propenyl) 8-oxo 5-thia 1-azabicyclo[4,2,0]oct-2-en-3-yl-2-carboxylate.

A suspension of 3.75 g of [[(diphenylmethoxy-carbonyl)]3,4-bis[(2-methoxy ethoxy) methoxy] phenyl] methoxy] imino] [2-[(triphenylmethyl) amino] 4-thiazolyl] acetic acid syn isomer (described in European Patent EP 238,061) and 1.81 g of p-methoxy-benzyl 7-amino-3-(3-chloropropenyl) 8-oxo 5-thia 1-azabicyclo [4,2,0] oct-2-en-2-carboxylate (prepared in European Patent EP 0 333,154) in dichloromethane was cooled down to 0° C., and 0.920 g of N—(dimethylaminopropyl) N'-ethyl carbodiimide hydrochloride were added. The solution was held at 0° C. with stirring for 30 minutes and the organic phase was washed with an aqueous solution of sodium chloride and dried. The solvents are eliminated and after chromatographing the residue on silica (eluant: methylene chloride—ether 85-15) and concretion in isopropyl ether, 4.546 g of the expected product were obtained.

NMR (CDCl$_3$ 400 MHz in ppm)
5.10 to 5.32: CO$_2$—C<u>H</u>$_2$—Ar (Ar: aromatic ring)
3.80: Ar—O—C<u>H</u>$_3$ Stage B: p-methoxy benzyl [6R-[3(E), 6-α, 7-β (Z)]] 7-[[[[(diphenylmethoxy carbonyl) [3,4-bis[(2-methoxy ethoxy) methoxy] phenyl] methoxy] imino] [2-(triphenylmethyl) amino] 4-thiazolyl] acetamido] 3-(3-iodo 1-propenyl) 8-oxo 5-thia 1-azabicyclo[4,2,0]oct-2-en-3-yl-2-carboxylate.

A mixture of the product of Step A, 10 ml of acetone and 341 mg of sodium iodide and approximately 10 mg of iodine was stirred for one hour at ambient temperature and the solvent was evaporated off. Then, the residue was taken up in 80 ml of dichloromethane, The organic phase was washed with an aqueous solution of sodium thiosulfate then with water. After drying, the solvents were eliminated and the residue was chromatographed on silica [eluant: dichloromethane—ethyl acetate (8-2)] to obtain 853 mg of the expected product.

NMR of the proton, (CDCl₃ 300 MHz)
6.9 to 7.35: —CH=CH—CH₂—I, Ar—H
6.13 (d,t J=15 and 8): —CH=CH—CH₂-I, E isomerism
4.0 (d): —CH=CH—CH₂—I
Stage C: (±)(cis) (Z) 7-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2(E)-propenyl] furo[2,3-b]pyridinium iodide.

1.928 g of the product prepared in Step B, 0.365 g of furo[2,3-b]pyridine and 2 ml of dichloromethane were stirred for two hours and 30 minutes and 40 ml of sulfuric ether were added. The precipitate was isolated, rinsed with ether, dried and chromatographed on silica eluting with a dichloromethane—methanol (92-8) mixture to obtain 0.5106 g of the expected product with a Rf=0.38
NMR of the proton (CDCl₃, 400 MHz, in ppm)
3.22 (s), 3.29 (s) and 3.35 (S): —O—CH₂—O—CH₂—CH₂—O—CH₃
3.79 (s): Ar—OCH₃
3.10 to 3.9: —S—CH₂—C(CH=CH—)=C— and —O—CH₂—O—CH₂—CH₂—O—CH₃
5.00 (d) and 5.04 (d): —CO—NH—CH(C=O)—CH(N—)—S—
5.15 to 5.35: —O—CH₂—O—CH₂—CH₂—O—CH₃
5.32 (s): —(C=O)—O—CH₂—Ar
5.79 (dd) and 5.85 (dd): —CO—NH—CH(C=O)—CH(N—)—S—
5.99 (resolved): Ar—CH(C=O)—O—
6.34 (m): —CH=CH—CH₂—N⁺
6.77 (resolved): —S—CH—C(C=N—)—N=
6.84 to 7.45: Ar—H, —CH=CH—CH₂—N⁺ and the H in position 3 of the furo[2,3-b]pyridinium
7.87 (m): H in position 5 of the furo[2,3-b]pyridinium 8.03 (m): H in position 2 of the furo[2,3-b]pyridinium 8.35 (d): the —NH—'s
8.66 (m): H in positions 4 and 6 of furo[2,3-b]pyridinium
Stage D: the internal salt of [6R-[3(E), 6-α, 7-β(Z)]] 7-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] furo[2,3-b]-pyridinium (R) or (S) or an (R+S) mixture, 0.516 g of the product of Step C and 5.1 ml of a solution of trifluoroacetic acid-with 10% anisole were stirred for 75 minutes and then 30 ml of sulfuric ether were added. The mixture was stirred for 90 minutes, followed by filtering, rinsing and drying to obtain 0.261 g of the desired product.
NMR of the proton (DMSO, 400 MHz, in ppm)
3.50 to 3.78 (m): —S—CH₃—C(CH=CH—)=C—
5.16 (d resolved): —CO—NH—CH(C=O)—CH(N—)—S—
5.31 (s): Ar—CH(C=O)—O—
5.58 (m): —CH=CH—CH₂—N⁺
5.77 (m): —CO—NH—CH(C=O)—CH(N—)—S—
6.32 (m): —CH=CH—CH₂—N⁺
6.65 to 6.80 (m): aromatic H's of the (3,4-dihydroxy phenyl) (Ar—H)
6.85 (s): —S—CH—C(C=N—)—N=
7.07 (d resolved): —CH=CH—CH₂—N⁺
7.52 (d): H in position 3 of the furo[2,3-b]pyridinium 7.98 (dd): H in position 5 of the furo[2,3-b]pyridinium 8.61 (d): H in position 2 of the furo[2,3-b]pyridinium 8.89 (dl) and 8.93 (d): H in positions 4 and 6 of the furo[2,3-b]pyridinium 7.31 (sl) (2 H) and 9.04 (m) (2 H): mobile H's
9.53 (d) and 9.61 (d): —CO—NH—CH(C=O)—CH(N—)—S—
EXAMPLE 25: The internal salt of [6R-[3(E), 6-α, 7-β (Z)]] 7-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] furo[3,2-b]-pyridinium (R) or (S) or an (R+S) mixture Using the procedure of Example 24, furo [3,2-b]pyridine as quaternization agent was reacted to obtain the desired product.
NMR of the proton (DMSO, 400 MHz, in ppm)
—S—CH₂—C(CH=CH—)=C— masked
5.14 (d resolved): —CO—NH—CH(C=O)—CH(N—)—S—
5.32 (s): Ar—CH(C=O)—O—
5.61 (m): —CH=CH—CH₂—N⁺
5.76 (m): —CO—NH—CH(C=O)—CH(N—)—S—
6.30 (m): —CH=CH—CH₂—N⁺ E. isomer
6.6 to 6.78 (m): Ar—H
6.86 (s): —S—CH—C(C=N—)—N=
7.02 (d resolved): —CH=CH—CH₂—N⁺
7.78 (sl): H in position 3 of the furo[3,2-b]pyridinium 8.06 (dd): H in position 6 of the furo[3,2-b]pyridinium 8.92 (d): H in position 2 of the furo[3,2-b]pyridinium 8.97 (d) to 9.04 (m): H in positions 5 and 7 of the furo [3,2-b]pyridinium 9.0 (m): mobile H's
9.48 (d) and 9.56 (d): —CO—NH—CH(C=O)—CH(N—)—S—
EXAMPLE 26: the internal salt of (8) (cis) (Z) 7-[3-[7-[[2-amino 4-thiazolyl) [[carboxy (3,4-dihydroxy phenyl) methoxy] imino] acetamido] 2-carboxy 8-oxo 5-thia 1-azabicyclo[4,2,0] oct-2-en-3-yl] 2 (E) -propenyl] thieno [2,3-b] pyridinium Using the procedure of Example 24, [[(S)-(diphenylmethoxycarbonyl) [3,4-bis[(2-methoxy ethoxy) methoxy] phenyl] methoxy] imino][2-[(triphenylmethyl) amino] 4-thiazolyl] acetic acid syn isomer (described in European Patents EP 0 266,060 and 0 280,521) and thieno [2,3-b]pyridine as quaternization agent were reacted to obtain the desired product with Rf=0.5 [thin layer chromatography (TLC); eluant: acetone—water (4-1)] and a specific rotation of $(\alpha)_D$=−11.5° [(c)=0.9 in DMSO],
NMR of the proton (DMSO, 400 MHz, in ppm
3.51 (m): —S—CH₂—C(CH=CH—)=C—
5.15 (d J=5): —CO—NH—CH(C=O)—CH(N—)—S—
5.32 (s): Ar—CH(C=O)—O—
5.67 (d, J=6): —CH=CH—CH₂—N⁺
5.8 (dd, sl after exchange): —CO—NH—CH(C=O)—CH(N—)—S—
6.27 (dt J=16 and 6): —CH=CH—CH₂—N⁺ E isomer
6.6 to 6.87 (m): Ar—H and—S—CH—C(C=N—)—N=
7.13 (d J=6): —CH=CH—CH₂—N⁺
7.89 (d): H in position 3 of the thieno[2,3-b]pyridinium 8.15 (dd): H in position 5 of the thieno[2,3-b]pyridinium 8.28 (d): H in position 2 of the thieno[2,3-b]pyridinium 9.08 (d): H in position 4 of the thieno[2,3-b]pyridinium 9.22 (d): H in position 6 of the thieno[2,3-b]pyridinium 9.55 (d): —CO—NH—CH(C=O)—CH (N—)—S—
EXAMPLE 27: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 4-methoxy pyridinium (R) or (S) or an (R+S) mixture, By operating in a similar manner to that of Example 1, using 4-methoxy pyridine as quaternization agent, the desired product is obtained.
NMR of the proton (DMSO, 400 MHz, in ppm)
3.72 (AB): —S—CH₂—C(CH=CH—)=C—
4.10 (s): Ar—O—CH₃
5.15 (d): —CO—NH—CH(C=O)—CH(N—)—S—
5.22 (l): —CH=CH—CH₂—N⁺

5.32 (s): Ar—C$\underline{H}$(C=O)—O—
5.77 (m) —CO—NH—CH(C=O)—CH(N—)—S—
6.25 (m) —CH=C$\underline{H}$—CH$_2$—N$^+$ E isomer
6.68 (dd), 6.74 (m) (2H) and 6.86 (s) (1H)=: Ar—$\underline{H}$ and —S—C$\underline{H}$—C(C=N—)—N=
6.95 (d J=15.5): —C$\underline{H}$=CH—CH$_2$—N$^+$
7.33: N$\underline{H}_2$
7.66 (d) and 8.83 (m): aromatic $\underline{H}$'s of 4-MeO pyridinium
9.0 (l), 9.5 (d) and 9.62 (d): mobile $\underline{H}$'s EXAMPLE 28: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 4-(methylthio) pyridinium (R+S), By operating in a similar manner to that of EXAMPLE 1 using 4-(methylthio) pyridine as quaternization agent, the desired product is obtained.
NMR of the proton (DMSO, 300 MHz, in ppm)
2.72 (s): Ar—S—C$\underline{H}_3$
5.15 (d) and 5.18 (d): —CO—NH—CH(C=O)—C$\underline{H}$(N—)—S—
5.22 (dl): —CH=CH—C$\underline{H}_2$—N$^+$
5.32 (s): Ar—C$\underline{H}$(C=O)—O—
5.77 (m, d resolved after exchange): —CO—NH—C$\underline{H}$(C=O)—CH(N—)—S—
6.26 (m): —CH=C$\underline{H}$—CH$_2$—N$^+$ E isomer
6.65 (dd) to 6.87 (m) (4 H)=: Ar—$\underline{H}$ and —S—C$\underline{H}$—C(C=N—)—N=
6.99 (d J=15 Hz): —C$\underline{H}$=CH—CH$_2$—N$^+$
7.96 (d) and 8.70 (d): aromatic $\underline{H}$'s of 4-Mes pyridinium
9.55 (d) and 9.62 (d): —CO—N$\underline{H}$—CH(C=O)—CH(N—)—S—
7.32 (m) and 9.06 (m): mobile $\underline{H}$'s EXAMPLE 29, the internal salt of [6R-[3(E), 6-α, 7-β [Z-(R*)]]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 4-(methylthio) pyridinium, Using the procedure of Example was purified by HPLC on a Microbondapack C$_{18-300}$ (registered trademark) column of 10 microns and 0.019 m in diameter eluting with acetonitrile with 0.025% trifluoroacetic acid to obtain the (R) and (S) isomers (See following example).
NMR of the proton (DMSO, 300 MHz, in ppm)
2.71 (s): Ar—S—C$\underline{H}_3$
3.54 (d) and 3.79 (d): —S—C$\underline{H}_2$—C(CH=CH—)=C—
5.17 (d): —CO—NH—CH(C=O)—C$\underline{H}$(N—)—S—
5.22 (l): —CH=CH—C$\underline{H}_2$—N$^+$
5.32 (s): Ar—C$\underline{H}$(C=O)—O—
5.77 (d, d): —CO—NH—C$\underline{H}$(C=O)—CH(N—)—S—
6.27 (m) : —CH=C$\underline{H}$—CH$_2$—N$^+$ E isomer
6.72 (d): $\underline{H}$ in position 5 of the (3,4-dihydroxy phenyl)
6.74 (s): —S—C$\underline{H}$—C(C=N—)—N=
6.73 (d): $\underline{H}$ in position 6 of the (3,4-dihydroxy phenyl)
6.86 (d): $\underline{H}$ in position 2 of the (3,4-dihydroxy phenyl)
6.98 (d J=15,5 Hz): —C$\underline{H}$=CH—CH$_2$—N$^+$
7.30 (l): —N$\underline{H}_2$
7.96 (d) and 8.71 (d): aromatic $\underline{H}$'s of 4-MeS pyridinium
9.62 (d): —CO—N$\underline{H}$—CH(C=O)—CH(N—)—S—
9.00 and 9.09: mobile $\underline{H}$'s EXAMPLE 30; the internal salt of [6R-[3(E), 6-α, 7-β [Z-(S*)]]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 4-(methylthio) pyridinium,
NMR of the proton (DMSO, 300 MHz, in ppm)
2.72 (s): Ar—S—C$\underline{H}_3$
3.54 [AB]: —S—C$\underline{H}_2$—C(CH=CH—)=C—
5.14 (d): —CO—NH—CH(C=O)—C$\underline{H}$(N—)—S—
5.22 (dl): —CH=CH—C$\underline{H}_2$—N$^+$
5.32 (s): Ar—C$\underline{H}$(C=O)—O—
5.79 (dd): —CO—NH—C$\underline{H}$(C=O)—CH(N—)—S—
6.24 (dt): —CH=C$\underline{H}$—CH$_2$—N$^+$ E isomer
6.65 to 6.78 (m) (3H) and 6.87 (1H): Ar—$\underline{H}$ and —S—C$\underline{H}$(C=N—)—N=
6.97 (d): —C$\underline{H}$=CH—CH$_2$—N$^+$
7.30 (l): —N$\underline{H}_2$
7.96 (d) and 8.70 (d): aromatic $\underline{H}$'s of 4-MeS pyridinium
9.55 (d): —CO—N$\underline{H}$—CH(C=O)—CH(N—)—S—
9.04 and 9.08: mobile $\underline{H}$'s EXAMPLE 31: The internal salt of [6R-[3(E), 6-α, 7-β (Z)]] 1-[3-[7-[[(2-amino 4-thiazolyl) [[carboxy (3,4-dihydroxy phenyl) methoxy] imino] acetyl] amino] 2-carboxy 8-oxo 5-thia 1-azabicyclo[4,2,0]oct-2-en-3-yl] 2-propenyl] 2-(methylthio) pyridinium (R) or (S) or an (R+S) mixture,
NMR of the proton (DMSO, 300 MHz, in ppm)
2.87 (s): Ar—S—C$\underline{H}_3$
5.16 (d, resolved): —CO—NH—CH(C=O)—C$\underline{H}$(N—)—S—
5.78 (d, resolved after exchange): —CO—NH—C$\underline{H}$(C=O)—CH(N—)—S—
6.13: —CH=C$\underline{H}$—CH$_2$—N$^+$ E isomer
6.65 to 6.80: Ar—$\underline{H}$
6.85: —S—C$\underline{H}$(C=N—)—N=
6.85 (d resolved): —C$\underline{H}$=CH—CH$_2$—N$^+$
7.32 and 9.05: —O$\underline{H}$
7.84 (t) and 8.44 (t): aromatic $\underline{H}$'s in position 3 and 4 of the 2-MeS pyridinium
8.04 (d): aromatic $\underline{H}$ in position 5 of the 2-MeS pyridinium
8.97 (d): aromatic $\underline{H}$ in position 2 of the 2-MeS pyridinium
9.57 (d resolved): —CO—N$\underline{H}$—CH(C=O)—CH(N—)—S—

EXAMPLE 32: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 4-(aminocarbonyl) pyridinium (R) or (S) or an (R+S) mixture,
NMR of the proton (DMSO, 300 MHz, in ppm)
3.50 to 3.75 (m): —S—C$\underline{H}_2$-C(CH=CH—)=C—
5.17 (d resolved): —CO—NH—CH(C=O)—C$\underline{H}$(N—)—S—
5.32 (s): Ar—C$\underline{H}$(C=O)—O—
5.44 (m): —CH=CH—C$\underline{H}_2$—N$^+$
5.77 (m): —CO—NH—C$\underline{H}$(C=O)—CH(N—)—S—
6.29 (m): —CH=C$\underline{H}$—CH$_2$—N$^+$ E isomer
6.66 to 6.78 (m) (3 H): Ar—$\underline{H}$
6.86 (s): —S—C$\underline{H}$(C=N—)—N=
7.06 (d, J=15.5): —C$\underline{H}$=CH—CH$_2$—N$^+$
8.44 (d): $\underline{H}$ in positions 3 and 5 of the pyridinium ring
8.67 (s) and 8.25 (s): (C=O)—N$\underline{H}_2$ slightly mobile
9.20 (d): $\underline{H}$ in positions 2 and 6 of the pyridinium ring
9.47 (d) and 9.54 (d): —CO—N$\underline{H}$—CH(C=O)—CH(N—)—S—
8.94 (m) (2 H) 7.24 (m) (2 H) and 12.85 (shoulder): mobile $\underline{H}$'s EXAMPLE 33: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl]4-(aminocarbonyl) pyridinium (R) or (S) or an (R+S) mixture-
NMR of the proton (DMSO, 300 MHz, in ppm)
3.50 to 3.80 (m): —S—C$\underline{H}_2$(CH=CH—)=C— masked
5.17 (d resolved): —CO—NH—CH(C=O)—C$\underline{H}$(N—)—S—

5.32 (s): Ar—C$\underline{H}$(C=O)—O—
5.44 (m): —CH=CH—C$\underline{H_2}$—N$^+$
5.77 (m): —CO—NH—C$\underline{H}$(C=O)—CH(N—)—S—
6.30 (m): —CH=C$\underline{H}$—CH$_2$—N$^+$ E isomer
6.64 to 6.90 (m) (4 H): Ar—$\underline{H}$ and—S—C$\underline{H}$(C=N—)—N=
7.08 (d J=15): —C$\underline{H}$=CH—CH$_2$—N$^+$
7.29 (3 H): =C—N$\underline{H_2}$
8.29 (t): $\underline{H}$ in position 5 of the pyridinium ring
8.36 (d): $\underline{H}$ in position 4 of the pyridinium ring
9.17 (d): $\underline{H}$ in position 6 of the pyridinium ring
9.47 (d): $\underline{H}$ in position 2 of the pyridinium ring
9.54 (d) and 9.62: —CO—N$\underline{H}$—CH(C=O)—CH(N—)—S—
8.20 (s) and 8.61 (s): slightly mobile $\underline{H}$'s 9.02: mobile $\underline{H}$'s
EXAMPLE 34: The internal salt of [6R-[3(E), 6-α, 7-β (Z)]] 6-amino 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] quinolinium (R) or (S) or an (R+S) mixture,
NMR of the proton (DMSO, 400 MHz, in ppm)
5.13: —CO—NH—CH(C=O)—C$\underline{H}$(N—)—S—
5.31 (d resolved): Ar—C$\underline{H}$(C=O)—O—
5.65 to 5.80: —CH=CH—C$\underline{H_2}$—N$^+$ and —CO—NH—C$\underline{H}$(C=O)—CH(N—)—S—
6.32 (m): —CH=C$\underline{H}$—CH$_2$—N$^+$ E isomer
6.65 to 7.0 (m) (5 H): Ar—$\underline{H}$, —S—C$\underline{H}$—C(C=N—)—N= and —C$\underline{H}$=CH—CH$_2$—N$^+$
7.56 (d resolved): $\underline{H}$ in position 7 of the quinolinium ring
7.88 (m): $\underline{H}$ in position 3 of the quinolinium ring
8.19 (m): $\underline{H}$ in position 8 of the quinolinium ring
8.80 (d): $\underline{H}$ in position 4 of the quinolinium ring 9.0 (s):
9.53 (d) and 9.61 (d): —CO—N$\underline{H}$—CH(C=O)—CH(N—)—S—
EXAMPLE 35: the internal salt of [6R-[3(E), 6-α, 7-β (Z)]] 3-amino 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] quinolinium (R) or (S) or an (R+S) mixture,
NMR of the proton (DMSO, 300 MHz, in ppm)
5.14: —CO—NH—CH(C=O)—C$\underline{H}$(N—)—S—
5.31 (s) and 5.32 (s): Ar—C$\underline{H}$(C=O)—O—
5.60 to 5.85 (m): —CH=CH—C$\underline{H_2}$—N$^+$ and —CO—NH—C$\underline{H}$(C=O)—CH(N—)—S—
6.33 (m): —CH=C$\underline{H}$—CH$_2$—N$^+$ E isomer
6.6 to 6.8 (m): Ar—$\underline{H}$,
6.86 (s): —S—C$\underline{H}$—C(C=N—)—N=
6.98 (d resolved): —C$\underline{H}$=CH—CH$_2$—N$^+$
7.76 (m) (2 H), 8.1 (m) (1 H) and 8.25 (m) (1 H): $\underline{H}$ in positions 5, 6, 7 and 8 of the quinolinium ring
8.03 (d): $\underline{H}$ in position 4 of the quinolinium ring
8.87 (sl): $\underline{H}$ in position 2 of the quinolinium ring
9.09 (m): mobile $\underline{H}$'s
9.53 (d) and 9.61 (d): —CO—N$\underline{H}$—CH(C=O)—CH(N—)—S—
EXAMPLE 36: the internal salt of [6R-[3 (E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 3-methyl quinolinium (R) or (S) or an (R+S) mixture,
NMR of the proton (DMSO, 300 MHz, in ppm)
2.66 (s): —C$\underline{H_3}$ in position 3 of the quinolinium ring
3,50 (masked) and 3.75 (d): —S—C$\underline{H_2}$(CH=CH—)=C—
5.13 resolved: —CO—NH—CH(C=O)—C$\underline{H}$(N—)—S—
5.31 (s): Ar—C$\underline{H}$(C=O)—O—
5.78 (m): —CO—NH—C$\underline{H}$(C=O)—CH(N—)—S—
5.85 (m): —CH=CH—C$\underline{H_2}$—N$^+$
6.36 (m): —CH=C$\underline{H}$—CH$_2$—N$^+$ E isomer
6.62 to 6.8 (m) (3 H): Ar—$\underline{H}$
6.85 (s): —S—C$\underline{H}$—C(C=N—)—N=
7.00 (d resolved): —C$\underline{H}$=CH—CH$_2$—N$^+$
8.01 (t) and 8.19 (t): $\underline{H}$ in position 6 and 7 of the quinolinium ring
8.38 (d) and 8.50 (d): $\underline{H}$ in position 5 and 8 of the quinolinium ring
9.14 (sl) and 9.54 (sl): $\underline{H}$ in position 2 and 4 of the quinolinium ring
9.04 (m): mobile $\underline{H}$'s
9.53 (d) and 9.59 (d): —CO—N$\underline{H}$—CH(C=O)—CH(N—)—S—
EXAMPLE 37: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 4-methyl quinolinium (R) or (S) or an (R+S) mixture,
NMR of the proton (DMSO, 300 MHz, in ppm)
3.02 (s): —C$\underline{H_3}$ in position 4 of the quinolinium ring
3.45 to 3.80 (m): —S—C$\underline{H_2}$—C(CH=CH—)=C—
5.13 (d resolved): —CO—NH—CH(C=O)—C$\underline{H}$(N—)—S—
5.31 (s): Ar—C$\underline{H}$(C=O)—O—
5.75 (d, resolved after exchange): —CO—NH—C$\underline{H}$(C=O)—CH(N—)—S—
5.80 (m): —CH=CH—C$\underline{H_2}$—N$^+$
6.37 (m): —CH=C$\underline{H}$—CH$_2$—N$^+$ E isomer
approximately 6.70 (m) (3 H): Ar—$\underline{H}$
6.85 (s): —S—C$\underline{H}$—C(C=N—)—N=
6.96 (d resolved j=16Hz): —C$\underline{H}$=CH—CH$_2$—N$^+$
8.06 (t) and 8.25 (t): $\underline{H}$ in position 6 and 7 of the quinolinium ring
8.11 (d): $\underline{H}$ in position 3 of the quinolinium ring
8.50 (2d): $\underline{H}$ in position 5 and 8 of the quinolinium ring
9.43 (d): $\underline{H}$ in position 2 of the quinolinium ring
7.30 (sl and 9.03 (sl): mobile $\underline{H}$'s (—N$\underline{H_2}$ and —O$\underline{H}$)
9.51 (d) and 9.59 (d): —CO—N$\underline{H}$—CH(C=O)—CH(N—)—S—
EXAMPLE 38: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 6-methyl quinolinium (R) or (S) or an (R+S) mixture,
NMR of the proton (DMSO, 300 MHz, in ppm)
2.62 (s): —C$\underline{H_3}$ in position 4of the quinoleinium ring
3.50 (masked) and 3.74 (d): —S—C$\underline{H_2}$—C(CH=CH—)=C—
5.13 (d resolved): —CO—NH—CH(C=O)—C$\underline{H}$(N—)—S—
5.31 (s): Ar—C$\underline{H}$(C=O)—O—
5.76 (d, resolved after exchange): —CO—NH—C$\underline{H}$(C=O)—CH(N—)—S—
5.86 (m): —CH=CH—C$\underline{H_2}$—N$^+$
6.35 (m): —CH=C$\underline{H}$—CH$_2$—N$^+$ E isomer
6.85 (s resolved): —S—C$\underline{H}$—C(C=N—)—N=
6.94 (d resolved j=16 Hz): —C$\underline{H}$=CH—CH$_2$—N$^+$
8.10 to 8.45 (m) (4 H): $\underline{H}$ in position 3, 5, 7 and 8 of the quinolinium ring
9.21 (d) (1 H): $\underline{H}$ in position 4 of the quinolinium ring
9.50 (d): $\underline{H}$ in position 2 of the quinolinium ring
9.03 (m): mobile $\underline{H}$'s
9.50 (d) and 9.60 (d): —CO—N$\underline{H}$—CH(C=O)—CH(N—)—S—
EXAMPLE 39: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 6-chloro quinolinium (R) or (S) or an (R+S) mixture,
NMR of the proton (DMSO, 300 MHz, in ppm)
3.60 (masked) and 3.75 (d) : —S—C$\underline{H}_2$(CH=CH—)=C—
5.14: —CO—NH—CH(C=O)—C$\underline{H}$(N—)—S—
5.31 (s): Ar—C$\underline{H}$(C=O)—O—
5.76 (m): —CO—NH—C$\underline{H}$(C=O)—CH(N—)—S—
5.88 (m): —CH=CH—C$\underline{H}_2$—N$^+$
6.34 (m): —CH=C$\underline{H}$—CH$_2$—N$^+$ E isomer
6.85 (s): —S—C$\underline{H}$—C(C=N—)—N=
6.96 (d resolved): —C$\underline{H}$=CH—CH$_2$—N$^+$
6.62 to 6.80 (m) (3 H): Ar—$\underline{H}$
8.29 (m) and 8.59 (dd): $\underline{H}$ in positions 3, 7 and 8 of the quinolinium ring
8.69 (d): $\underline{H}$ in position 5 of the quinolinium ring
9.25 (d): $\underline{H}$ in position 4 of the quinolinium ring
9.59 (d); $\underline{H}$ in position 2 of the quinoleinium ring
9.04 (m) mobile $\underline{H}$'s
9.52 (d) and 9.60 (d): —CO—N$\underline{H}$—CH(C=O)—CH(N—)—S—

EXAMPLE 40: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 6-methoxy quinolinium (R) or (S) or an (R+S) mixture,
NMR of the proton (DMSO, 400 MHz, in ppm)
3.45 to 3.75 (m): —S—C$\underline{H}_2$—C(CH=CH—)=C—
4.00 (s): —OC$\underline{H}_3$ in position 6 of the quinolinium ring
5.12 (d resolved): —CO—NH—CH(C=O)—C$\underline{H}$(N—)—S—
5.31 (s): Ar—C$\underline{H}$(C=O)—O—
5.74 (dd resolved): —CO—NH—C$\underline{H}$(C=O)—CH(N—)—S—
5.84 (m): —CH=CH—C$\underline{H}_2$—N$^+$
6.35 (m): —CH=C$\underline{H}$—CH$_2$—N$^+$ E isomer
6.65 to 6.80 (m): Ar—$\underline{H}$
6.85 (s): —S—C$\underline{H}$—C(C=N—)—N=
6.93 (d resolved J=16 Hz): —C$\underline{H}$=CH—CH$_2$—N$^+$
7.89 (dd): $\underline{H}$ in position 7 of the quinolinium ring
7.90 (sl): $\underline{H}$ in position 5 of the quinolinium ring
8.15 (dd): $\underline{H}$ in position 3 of the quinolinium ring
8.46 (dd): $\underline{H}$ in position 4 of the quinolinium ring
9.13 (d): $\underline{H}$ in position 8 of the quinolinium ring
9.37 (d): $\underline{H}$ in position 2 of the quinolinium ring
7.27 (m) (2 H) and 8.94 (m) (2 H): mobile $\underline{H}$'s
9.45 (d) and 9.52 (d): —CO—N$\underline{H}$—CH(C=O)—CH(N—)—S EXAMPLE 41: the internal salt of [6R-[3(E), 6-α, 7-β (Z)]] 3-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] thiazolium (R) or (S) or an (R+S) mixture,
NMR of the proton (DMSO, 400 MHz, in ppm)
3.40 3.80 (m): —S—C$\underline{H}_2$—C(CH=CH—)=C—
5.16 (d resolved): —CO—NH—CH(C=O)—C$\underline{H}$(N—)—S—
5.33 (m) (3 H): Ar—C$\underline{H}$(C=O)—O— and —CH=CH—C$\underline{H}_2$—N$^+$
5.77 (m): —CO—NH—C$\underline{H}$(C=O)—CH(N—)—S—
6.26 (m): —CH=C$\underline{H}$—CH$_2$—N$^+$ E isomer
6.65 to 6.77 (m): Ar—$\underline{H}$
6.87 (s): —S—C$\underline{H}$—C(C=N—)—N=
6.97 (d resolved): —C$\underline{H}$=CH—CH$_2$—N$^+$
7.30 (s) (2 H): mobile $\underline{H}$'s
8.36 (s) and 8.52 (s): $\underline{H}$ in position 4 and 5 of the thiazolium ring
9.00 (s), 9.08 (s), 9.09 (s) and 9.64 (s): mobile 2 $\underline{H}$'s
9.54 (d) and 9.62 (d): —CO—N$\underline{H}$—CH(C=O)—CH(N—)—S—
10.21 (s): $\underline{H}$ in position 2 of the thiazolium ring EXAMPLE 42: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 3-methyl imidazolium (R) or (S) or an (R+S) mixture,
NMR of the proton (DMSO, 400 MHz, in ppm)
3.50 to 3.80: —S—C$\underline{H}_2$—C(CH=CH—)=C—
3.86 (s): —C$\underline{H}_3$ in position 3 of the imidazolium ring
4.97 (d): —CH=CH—C$\underline{H}_2$—N$^+$
5.16 (d resolved): —CO—NH—CH (C=O)—C$\underline{H}$(N—)—S—
5.33 (s): Ar—C$\underline{H}$(C=O)—O—
5.79 (m): —CO—NH—C$\underline{H}$(C=O)—CH(N—)—S—
6.18 (m): —CH=C$\underline{H}$—CH$_2$—N$^+$ E isomer
6.75 to 7.00 (m): Ar—$\underline{H}$, —S—C$\underline{H}$—C(C=N—)—N= and —C$\underline{H}$=CH—CH$_2$—N$^+$
7.28: N$\underline{H}_2$
7.71 (s) (2 H): $\underline{H}$ in position 2 and 3 of the imidazolium ring
8.96 (wide), 12.81 (wide) and 13.68 (wide): mobile 2 $\underline{H}$'s
9.12 (s): $\underline{H}$ in position 5 of the imidazolium ring
9.47 (d) and 9.54 (d): —CO—N$\underline{H}$—CH(C=O)—CH(N—)—S—

EXAMPLE 43: the internal salt of (±) (cis) (Z) 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2(E)-propenyl] imidazo[1,2-b] pyridazinium (R) or (S) or an (R+S) mixture,
NMR of the proton (DMSO, 400 MHz, in ppm)
(1 H) masked and approximately 3.70 (d) (1 H): —S—C$\underline{H}_2$—C(CH=CH—)=C—
5.15 (d resolved): —CO—NH—CH(C=O)—C$\underline{H}$(N—)—S—
5.25 to 5.45 (m): —CH=CH—C$\underline{H}_2$—N$^+$ and Ar—C$\underline{H}$(C=O)—O—
5.77 (m, d resolved after exchange): —CO—NH—C$\underline{H}$(C=O)—CH(N—)—S—
6.25 (m): —CH=C$\underline{H}$—CH$_2$—N$^+$ E isomer
6.65 to 6.86 (m): Ar—$\underline{H}$ and —S—C$\underline{H}$—C(C=N—)—N=
6.96 (dl J=16 Hz): —C$\underline{H}$=CH—CH$_2$—N$^+$
7.34 (m) and 9.05 (m): mobile $\underline{H}$'s
8.00 (dd): $\underline{H}$ in position 3 of the imidazo[1,2-b]pyridazinium ring
8.54 (sl) and 8.88 (sl): $\underline{H}$ in position 6 and 7 of the imidazo[1,2-b]pyridazinium ring
8.82 (d): $\underline{H}$ in position 4 of the imidazo]1,2-b]pyridazinium ring
9.12 (d): $\underline{H}$ in position 2 of the imidazo[1,2-b]pyridazinium ring
9.55 (d) and 9.60 (d): —CO—N$\underline{H}$—CH(C=O)—CH(N—)—S—

EXAMPLE 44: the internal salt of (±) (cis) (Z) 1-[3-[7--[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2 (E)-propenyl] imidazo-[1,2-a]pyridinium (R) or (S) or an (R+S) mixture,
NMR of the proton (DMSO, 300 MHz, in ppm)
3.55 (m) (masked): —S—C$\underline{H}_2$—C(CH=CH—)=C—
5.15 (m): —CO—NH—CH(C=O)—C$\underline{H}$(N—)—S—
5.29 (m): —CH=CH—C$\underline{H}_2$—N$^+$
5.32 (s): Ar—C$\underline{H}$(C=O)—O—
5.74 (m): —CO—NH—C$\underline{H}$(C=O)—CH(N—)—S— cis isomerism
6.25 (m): —CH=C$\underline{H}$—CH$_2$—N$^+$ E isomer
6.68 to 6.92: Ar—$\underline{H}$, —S—C$\underline{H}$—C(C=N—)—N= and —C$\underline{H}$=CH—CH$_2$—N$^+$
7.33 (s) , 9.03 (s), 9.56 (d resolved) and 12.80: mobile $\underline{H}$'s 7.57 (t) (1 H), 8.06 (t) (1 H), 8.20 (d) (1 H), 8.29 (s) (1 H), 8.45 (s) (1 H) and 8.97 (d) (1 H): H of the imidazo [1,2-b]pyridinium ring EXAMPLE 45: The internal salt of (±) (cis) (Z) 2-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2(E)-propenyl] imidazo-[1,5-a]pyridinium (R) or (S) or an (R+S) mixture, NMR of the proton (DMSO, 300 MHz, in ppm)
3.40 to 3.80: —S—CH$_2$—C(CH=CH—)=C—
5.17 (m): —CO—NH—CH(C=O)—CH(N—)—S—
5.18 to 5.32: —CH=CH—CH$_2$—N$^+$ and Ar—C H(C=O)—O—
5.76 (m): —CO—NH—CH(C=O)—CH(N—)—S— cis isomerism
6.28 (m): —CH=CH—CH$_2$—N$^+$ E isomer
6.68 to 6.86: Ar—H and —S—CH—C(C=N—)—N=
7.04 (d J=15.5): —CH=CH—CH$_2$—N$^+$
7.29, 9.0 to 9.08, 9.54 and 12.56: mobile H's
7.19 (t) and 7.25 (t): H in position 6 and 7 of the imidazo [1,5-a]pyridinium ring
7.86 (d): H in position 8 of the imidazo[1,5-a]pyridinium ring8.23 (d): H in position 1 of the imidazo[1,5-a] pyridinium ring
9.02 (d): H in position 5 of the imidazo [1,5-a]pyridinium ring
9.74 (s): H in position 3 of the imidazo [1,5-a]pyridinium ring EXAMPLE 46: The internal salt of [6R-[3(E), 6-α, 7-β [Z(R*)]]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2(E)-propenyl] 6,7-dihydro 5H—pyrindinium, Stage A: The internal salt of [6R-[3(E), 6-α, 7-β (Z)]] 1-[3-[7-[[[[(diphenylmethoxycarbonyl) [3,4-bis[(2-methoxy ethoxy) methoxy] phenyl] methoxy] imino] [2-(triphenylmethyl) amino] 4-thiazolyl] acetamido] 2-carboxy 8-oxo 5-thia 1-azabicyclo[4,2,0]oct-2-en-3-yl] 2(E)-propenyl] 6,7-dihydro 5H—pyrindinium, (R+S)

1.33 g of the iodine derivative of Step B of Example 24 and 0.585 ml of cyclopentano[b]pyridine in a minimum quantity of dimethylsulfoxide (DMSO) were stirred for 5 hours and the solvent was eliminated. The residue was washed and chromatographed, eluting with a dichloromethane—methanol (9-1) mixture to obtain in this way 1.07 g of the desired product.

Stage B: The internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2(E)-propenyl] 6,7-dihydro 5H—pyrindinium, Using the procedure of Step D of Example 24, 1.053 g of the product of Step A were reacted to obtain 1.07 g of the expected product.

Stage C: The internal salt of [6R-[3(E), 6-α, 7-β [Z(R*)]]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2(E)-propenyl] 6,7-dihydro 5H—pyrindinium, The product of Step B was purified by HPLC on a Microbondapack C$_{18-300}$ (registered trademark) column of 10 microns and 0.0079 m in diameter eluting with acetonitrile with 0.025% of trifluoroacetic acid to obtain the (R) and (S) isomers (See following example).

NMR of the proton (DMSO, 400 MHz, in ppm)
2.24 (m): the H's in position 6 of the 6,7-dihydro 5H-pyrindinium ring
3.15 (m) and 3.38 (masked): the H's in position 5 and 7 of the 6,7-dihydro 5H—pyrindinium ring
3.54 (d, J=17.5 Hz) and 3.78 (d, J=17.5 Hz): —S—C H$_2$—C(CH=CH—)=C—
5.17 (d, J=5): —CO—NH—CH(C=O)—CH(N—)—S—
5.32 (m): —CH=CH—CH$_2$—N$^+$ and Ar—C H(C=O)—O—
5.75 (dd, J=5 Hz and J=7.5 Hz): —CO—NH—C H(C=O)—CH(N—)—S—
6.24 (dt, J=16 and J=6.5 Hz): —CH=CH—CH$_2$—N$^+$ E isomer
6.70 (d, J=8 Hz): H in position 6 of the 3,4-dihyroxyphenyl radical
6.74 (s): —S—CH—C(C=N—)—N=
6.75 (dd, J=1.5 and J=8 Hz): H in position 5 of the 3,4-dihydroxyphenyl radical
6.86 (sl): H in position 2 of the 3,4-dihydroxyphenyl radical
6.87 (d J=16): —CH=CH—CH$_2$—N$^+$
7.25: Mobile NH$_2$'s
7.90 (dd, J=6 and J=7.5): H in position 3 of the 6,7-dihydro 5H—pyrindinium ring
8.41 (d, J=7.5): H in position 4 of the 6,7-dihydro 5H-pyrindinium ring
8.75 (d, J=6): H in position 2 of the 6,7-dihydro 5H-pyrindinium ring
9.53 (d, J=7.5Hz): —CO—N H—CH(C=O)—CH(N—)—S—
8.92, 9.00, 12.76 and 13.72: mobile H's EXAMPLE 47: The internal salt of [6R-[3(E), 6-α, 7-β [Z(S*)]]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2(E)-propenyl] 6,7-dihydro 5H—pyrindinium, NMR of the proton (DMSO, 400 MHz, in ppm)
2.24 (m): the H's in position 6 of the 6,7-dihydro 5H-pyrindinium ring
3.15 (m) and 3.40: the H's in position 5 and 7 of the 6,7-dihydro 5H—pyrindinium ring
3.48 (d, J=17.5 Hz) and 3.63 (d, J=17.5 Hz): —S—C H$_2$—C(CH=CH—)=C—
5.14 (d, J=5): —CO—NH—CH(C=O)—CH(N—)—S—
5.32 (m): —CH=CH—CH$_2$—N+ and Ar—C H(C=O)—O—
5.78 (dd, J=5 Hz and J=7.5 Hz): —CO—NH—C H(C=O)—CH(N—)—S—
6.20 (dt, J=16 and J=6 Hz): —CH=CH—CH$_2$—N$^+$ E isomer
6.68 (d, J=8 Hz): H in position 6 of the 3,4-dihyroxyphenyl radical
6.75 (dd, J=2 and J=8 Hz) : H in position 5 of the 3,4-dihydroxyphenyl radical
6.78 (s): —S—CH—C(C=N—)—N=
6.87 (d. J=2 Hz): H in position 2 of the 3,4-dihydroxyphenyl radical6.87 (d J=16): —CH=CH—CH$_2$—N$^+$
7.25: mobile NH$_2$'s
7.90 (dd, J=6 and J=7.5): H in position 3 of the 6,7-dihydro 5H—pyrindinium ring
8.42 (d, J=7.5): H in position 4 of the 6,7-dihydro 5H-pyrindinium ring
8.75 (d, J=6): H in position 2 of the 6,7-dihydro 5H-pyrindinium ring
9.46 (d, J=7.5 Hz): —CO—N H—CH(C=O)—CH(N—)—S—
8.98 (2 H), 9.00, 12.97 (1 H) and 13.69 (1 H): mobile H's EXAMPLE 48: the internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 4-[(methoxyimino) methyl] quinoleinium (R) or (S) or an (R+S) mixture,
NMR of the proton (DMSO, 300 MHz, in ppm)
3.47 (m): —S—CH$_2$—C(CH=CH—)=C—
4.19 (s): —CH=N—OCH$_3$ in position 4 of the quinolinium ring
5.14 (m): —CO—NH—CH(C=O)—CH—(N—)—S—
5.31 (s): Ar—CH(C=O)—O—
5.75 (m): —CO—NH—CH(C=O)—CH(N—)—S—
5.89 (m): —CH=CH—CH$_2$—N$^+$
6.36 (m): —CH=CH—CH$_2$—N$^+$ E isomer
6.64 to 6.77 (m): Ar—H
6.85 (s,d): —S—CH—C(C=N—)—N=
6.99 (d resolved j=16 Hz): —CH=CH—CH$_2$—N$^+$
7.31 (1): —NH$_2$
8.09 (1) and 8.30 (t): H in position 6 and 7 of the quinolinium ring 8.41 (d): H in position 3 of the quinolinium ring
8.58 (d) and 8.96 (d): H in position 5 and 8 of the quinolinium ring 9.33 (s): —CH=N—OCH$_3$ in position 4 of the quinolinium ring (E isomer)
9.52 (d,d): H in position 2 of the quinolinium ring 9.03 (1) and 9.60 (d): mobile H's EXAMPLE 49: the internal salt of (±) (cis) (Z) 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2(E)-propenyl] 1-methyl pyrrolidinium (R) or (S) or an (R+S) mixture,
NMR of the proton (DMSO, 300 MHz, in ppm)
2.10 (sl) and 3.45 (sl): H of the pyrrolidinium ring
2.99 (s): N$^+$—CH$_3$
3.9 (m): —S—CH$_2$—C(CH=CH—)=C—
4.11: —CH=CH—CH$_2$—N$^+$
5.18 (m): —CO—NH—CH(C=O)—CH(N—)—S—
5.33 (s): Ar—CH(C=O)—O—
5.79 (m): —CO—NH—CH(C=O)—CH(N—)—S—
6.17 (dt): —CH=CH—CH$_2$—N$^+$ E isomer
6.65 to 6.85: Ar—H and —S—CH—C(C=N—)—N=
7.05 (d. J=15 Hz): —CH=CH—CH$_2$—N$^+$ EXAMPLE 50: the internal salt of [6R-[3(E), 6-α, 7-β (Z)]] 1-[3 [7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 4-aza 1-azoniabicyclo[2,2,2]octane (R) or (S) or an (R+S) mixture,
NMR of the proton (DMSO, 300 MHz, in ppm)
3.14 and 3.35: H of the 4-aza 1-azoniabicyclo[2,2,2]octane ring
3.5 to 3.95: —S—CH$_2$-C(CH=CH—)=C—
4.06: —CH=CH—CH$_2$—N$^+$
5.20 (d, resolved): —CO—NH—CH(C=O)—CH(N—)—S—
5.34 (s): Ar—CH(C=O)—O—
5.80 (d, resolved): —CO—NH—CH(C=O)—CH(N—)—S—
6.11: —CH=CH—CH$_2$—N$^+$ E isomer
6.7 to 6.90: Ar—H and —S—CH—C(C=N—)—N=
7.02 (d, resolved): —CH=CH—CH$_2$—N$^+$
9.10 (d resolved): —CO—NH—CH(C=O)—CH(N—)—S—

EXAMPLE 51: The internal salt of [6R-[3(E), 6-α, 7-β (Z)]] 1-[3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] 2-propenyl] 3-hydroxy 4-aza 1-azoniabicyclo[2,2,2]octane (R) or (S) or an (R+S) mixture with an Rf=0.5 (eluant: acetone—water (4-1))

EXAMPLE 52: The internal salt of (±) (cis) (Z) 3-[7-[[(2-amino 4-thiazolyl) [carboxy (3,4-dihydroxy phenyl) methoxy] imino] acetamido] 2-carboxy 8-oxo 5-thia 1-azabicyclo[4,2,0] oct-2-3-yl] N,N,N-trimethyl 2(E)-propen-1-aminium (R) or (S) or an (R+S) mixture,
NMR of the proton (DMSO, 300 MHz, in ppm)
2.99 (s) and 3.03 (s): —N$^+$ (CH$_3$)$_3$
4.05: —CH=CH—CH$_2$—N$^+$
5.16 (d): —CO—NH—CH(C=O)—CH(N—)—S—
5.33 (s): Ar—CH(C=O)—O—
5.76 (d): —CO—NH—CH(C=O)—CH(N—)—S—
6.04 (m): —CH=CH—CH$_2$—N$^+$ E isomer
6.7 to 6.90: Ar—H and —S—CH—C(C=N—)—N=
7.04 (d, resolved): —CH=CH—CH$_2$—N$^+$
9.08 (d resolved): —CO—NH—CH(C=O)—CH(N—)—S—

EXAMPLE 53: The internal salt of [6R-[3(E), 6-α, 7-β (Z)]] 3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] N,N—dimethyl N—(2-hydroxy ethyl) 2-propen-1-aminium (R) or (S) or an (R+S) mixture,
NMR of the proton (DMSO, 300 MHz, in ppm)
3.05 (s): —N$^+$ (CH$_3$)$_2$—CH$_2$—CH$_2$—OH
3.38 and 3.87: —N$^+$ (CH$_3$)$_2$—CH$_2$—CH$_2$—OH
4.14 (d): —CH=CH—CH$_2$—N$^+$
5.19 (d, resolved): —CO—NH—CH(C=O)—CH(N—)—S—
5.80 (d, resolved): —CO—NH—CH(C=O)—CH(N—)—S—
6.14: —CH=CH—CH$_2$—N$^+$ E isomer
6.87: —S—CH—C(C=N—)—N=
6.65 to 6.80: Ar—H
7.03 (d, resolved): —CH=CH—CH$_2$—N$^+$
7.36 and 9.05: —OH
9.59 (d resolved): —CO—NH—CH(C=O)—CH(N—)—S—

EXAMPLE 54: The internal salt of (±) (cis) (Z) N—(2-amino 2-oxo ethyl) 3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] N,N—dimethyl 2(E)-propen-1-aminium (R) or (s) or an (R+S) mixture,
NMR of the proton (DMSO 300 MHz, in ppm)
3.19 (s): —N$^+$(CH$_3$)$_2$—CH$_2$—CO —NH$_2$
4.01 (s): —N$^+$(CH$_3$)$_2$—CH$_2$—CO—NH$_2$
4.27 (d): —CH=CH—CH$_2$—N$^+$
5.19 (d): —CO—NH—CH (C=O)—CH(N—)—S—
5.34 (s): Ar—CH(C=O)—O—
5.85 (m): —CO—NH—CH(C=O)—CH(N—)—S—
6.13: —CH=CH—CH$_2$—N$^+$ E isomer
6.72 to 6.80: Ar—H and —S—CH—C(C=N—)—N=
7.03: —CH=CH—CH$_2$—N$^+$
7.33, 7.70, 7.94 and 9.04: mobile H's
9.55 (d) and 9.62 (d): —NH—

EXAMPLE 55: the internal salt of (±) (cis) (Z) 3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]oct-2-en-3-yl] N—(cyanomethyl) N,N—dimethyl 2(E)-propen-1-aminium (R) or (S) or an (R+S) mixture,
NMR of the proton (DMSO, 300 MHz, in ppm)
3.19 (s): —N$^+$(CH$_3$) $_2$—CH$_2$—CN
4.24 (d): —CH=CH—CH$_2$—N$^+$
4.8 (s): —N$^+$(CH$_3$)$_2$—CH$_2$—CN
5.20 (d): —CO—NH—CH(C=O)—CH(N—)—S—
5.33 (s): Ar—CH(C=O)—O—
5.82 (m): —CO—NH—CH(C=O)—CH(N—)—S—
6.13 (m): —CH=CH—CH$_2$—N$^+$ E isomer 6.65 to 6.80: Ar—H
6.87: —S—CH—C(C=N—)—N=
7.10: —CH=CH—CH$_2$—N$^+$
7.79 (2 H), 9.07 (2 H): mobile H's
9.54 (d): —CO—NH—CH(C=O)—CH(N—)—S—
EXAMPLE 56: The internal salt of (±) (cis) (Z) 3-[7-[[(2-amino 4-thiazolyl) [carboxy (3,4-dihydroxy phenyl) methoxy] imino] acetamido] 2-carboxy 8-oxo 5-thia 1-azabicyclo[4,2,0]-oct-2-en-3-yl] N,N—dimethyl N—[(2-methoxyimino) ethyl] 2(E)-propen-1-aminium (R) or (S) or an (R+S) mixture,
NMR of the proton (DMSO, 300 MHz, in ppm)
3.19 (s): —N$^+$(CH$_3$)$_2$—CH$_2$—CH=N—O—CH$_3$
3.89 (s): —N$^+$(CH$_3$)$_2$—CH$_2$—CH=N—O—CH$_3$
4.10 to 4.30 (m): —CH=CH—CH$_2$—N$^+$ and —N$^+$(CH$_3$)$_2$—CH$_2$—CH=N—O—CH$_3$
5.20 (d): —CO—NH—CH(C=O)—CH(N—)—S—
5.35 (s): Ar—CH(C=O)—O—
5.81 (m,d resolved after exchange); —CO—NH—CH(C=O)—CH(N—)—S—
6.14 (m): —CH=CH—CH$_2$—N$^+$ E isomer
6.7 to 6.88: Ar—H and —S—CH—C(C=N—)—N=
7.04: —CH=CH—CH$_2$—N$^+$
7.77 (m): —N$^+$(CH$_3$)$_2$—CH$_2$—CH=N—O—CH$_3$
9.57 and 9.65: —CO—NH—CH(C=O)—CH(N—)—S—
EXAMPLE 57: the internal salt of (±) (cis) (Z) 1-[3—[7--[[(2-amino 4-thiazolyl) [carboxy (3,4-dihydroxy phenyl) methoxy) imino] acetamido] 2-carboxy 8-oxo 5-thia 1-azabicyclo[4,2,0]oct-2-en-3-yl] 2(E)-propenyl] imidazo [1,2-a] pyrimidin-4-ium (R) or (S) or an (R+S) mixture,
NMR of the proton (DMSO, 300 MHz, in ppm)
3.66 (m) (masked): —S—CH$_2$—C(CH=CH—)=C—
5.14 (d, resolved): —CO—NH—CH(C=O)—CH(N—)—S—
5.24 (m): —CH=CH—CH$_2$—N$^+$
5.31 (s): Ar—CH(C=O)—O—
5.74 (m): —CO—NH—CH(C=O)—CH(N—)—S— cis isomerism
6.23 (m): —CH=CH—CH$_2$—N$^+$ E isomer
6.65 to 6.84 (4 H): Ar—H, and —S—CH—C(C=N—)—N=
6.94 (d, resolved J=16): —CH=CH—CH$_2$—N$^+$
7.31 (sl): —NH2
9.03 (m): mobile H's
7.76 (dd) (1 H): H in position 6 of the imidazo[1,2-a]-pyrimidin-4-ium ring
8.39 (s): H in position 2 and 3 of the imidazo[1,2-a]-pyrimidin-4-ium ring
9.14 (d, resolved) (1 H): H in position 7 of the imidazo[1,2-a]pyrimidin-4-ium ring
9.39 (d, resolved) (1 H): H in position 5 of the imidazo[1,2-a]pyrimidin-4-ium ring Unless otherwise indicated, the products of Examples 30 to 58 mentioned previously were prepared by the method described in Example 1, using the corresponding nitrogenous base.

EXAMPLE 58: Preparations for injections of the following formula were prepared from 500 ml of the product of Example 30 and sterile aqueous excipient sufficient for a quantity of sterile aqueous excipient sufficient quantity of 5 ml

EXAMPLE 59

A preparation for injection was prepared containing 500 mg of the product of Example 2 and sterile aqueous excipient sufficient for a final volume of 5 ml.

PHARMACOLOGICAL STUDY

In vitro activity, method of dilutions in solid medium.

A series of dishes was prepared into which an equal amount of sterile nutritive medium was divided containing increasing quantities of the product to be studied and then each dish was seeded with several bacterial strains. After incubation for 24 hours in an oven at 37° C., the inhibition of growth was evaluated by the absence of any bacterial development which allowed the minimal inhibiting concentrations (MIC), expressed in micrograms and, to be determined. The results are expressed in MIC$_{90}$, which is the minimum concentration of antibiotic enabling the inhibition of 90% of the strains studied in the following Table.

PHARMACOLOGICAL STUDY OF THE PRODUCTS OF THE INVENTION

Activity in vitro, method of dilutions in solid medium.

A series of dishes are prepared in which the same quantity of sterile nutrient medium is distributed, containing increasing quantities of the product to be studied, then each dish is sown with several bacterial strains.

After incubation for 24 hours in an incubator at 37° C., the growth inhibition is evaluated by the absence of any bacterial development, which allows the minimum inhibiting concentrations (MIC) expressed in micrograms/cm$^3$ to be determined.

The results are expressed in MIC$_{90}$ which is the minimum concentration of antibiotic causing growth inhibition in 90% of the strains studied.

The following results were obtained:

| Product of Example | Enterobacteries Cloacae 1321E | Staphylococcus aureus SG 5 11 | Proteus A 235 | Pseudomonas Aeruginosa 1771 m |
|---|---|---|---|---|
| 28 | 0.08 | 0.15 | 0.04 | 0.3 |
| 30 | 0.04 | 0.15 | 0.02 | 0.6 |
| 24 | 0.15 | 0.15 | 0.02 | 0.15 |
| 44 | 0.15 | 0.15 | 0.04 | 0.6 |

| | Number of strains | | | | |
|---|---|---|---|---|---|
| | Enterobacteria | | Staphylococcus aureus | | Pseudomonas |
| Compound example | Cefotax.S 27 | Cefotax.R 40 | oxacilline S 20 | Proteus SPP 9 | Aeruginosa 40 |
| 2 | 0.3 | 5 | 0.6 | 0.15 | 1.25 |
| 4 | 0.3 | 5 | 1.25 | 0.3 | 5 |
| 9 | 0.6 | 10 | 1.2 | 0.6 | 2.5 |
| 12 | 0.3 | 10 | 0.6 | 0.3 | 10 |

-continued

| | Number of strains | | | | |
|---|---|---|---|---|---|
| | Enterobacteria | | Staphylococcus aureus | | Pseudomonas |
| Compound example | Cefotax.S 27 | Cefotax.R 40 | oxacilline S 20 | Proteus SPP 9 | Aeruginosa 40 |
| 16 | 0.6 | 10 | 1.2 | 0.6 | 2.5 |
| 17 | 0.6 | 10 | 1.2 | 0.6 | 1.2 |
| 18 | 0.15 | 2.5 | 0.3 | 0.3 | 2.5 |

Various modifications of the compounds and method of the invention may be made without departing from the spirit or scope thereof and it should be understood that the invention is intended to be limited only as defined in the appended claims.

What we claim is:

1. A compound having a formula

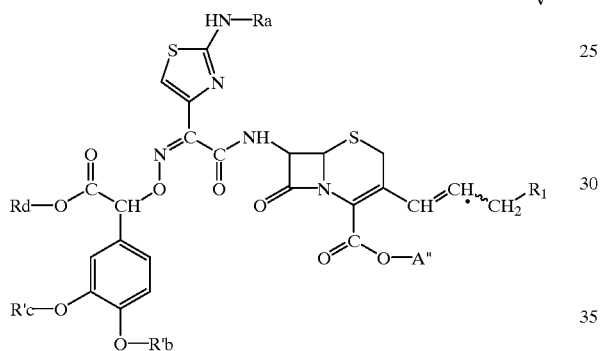

wherein $R_a$ is an amino protective group, $R'_b$ and $R'_c$ are individually hydrogen or a hydroxy protective group, $R_d$ is hydrogen or an easily eliminated ester, A" is hydrogen or an easily eliminated ester, $R_1$ is selected from the group consisting of

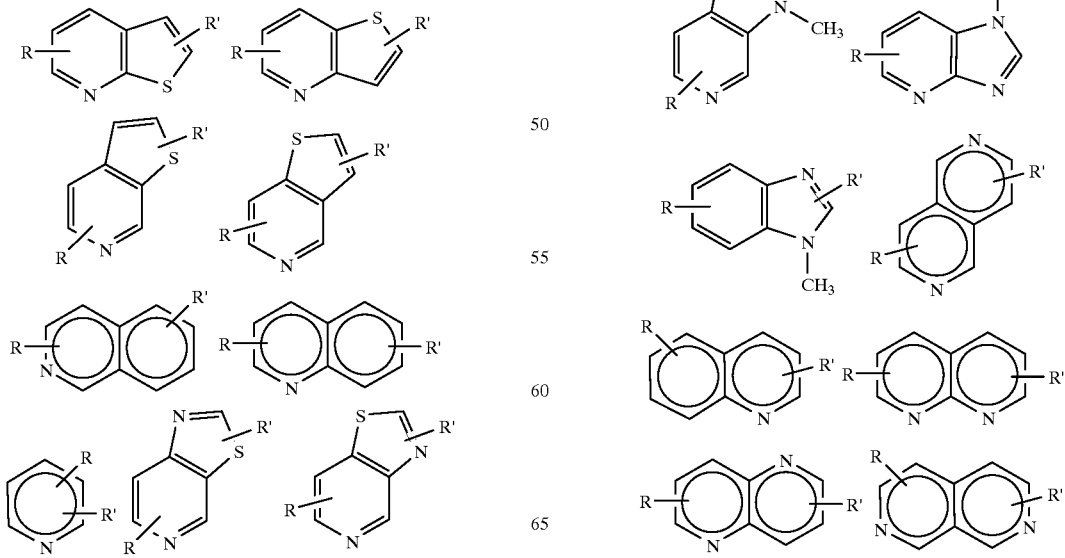

-continued
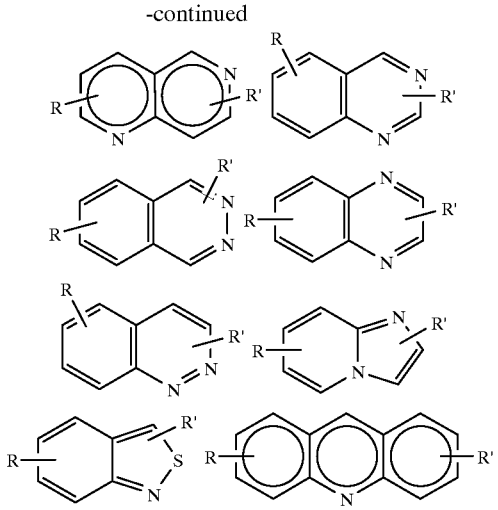
R and R' are individually selected from the group consisting of hydrogen, alkyl of 1 to 4 carbon atoms, alkoxy of 1 to 4 carbon atoms, halogen, $-CO_2-Q$,
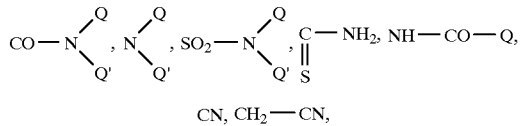
$-CH_2SQ$, Q and Q' are individually hydrogen or alkyl of 1 to 4 carbon atoms, the wavy line indicated that $-CH_2R_1$ may be in the E or Z position.
* * * * *